(12) United States Patent
Ledesma et al.

(10) Patent No.: US 6,582,417 B1
(45) Date of Patent: Jun. 24, 2003

(54) METHODS AND APPARATUSES FOR RADIATION TREATMENT

(75) Inventors: Michelle N. Ledesma, Houston, TX (US); Anthony J. Bradshaw, Sugar Land, TX (US); Richard T. Thornton, League City, TX (US); J. Eric Henckel, Houston, TX (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/505,367

(22) Filed: Feb. 16, 2000

Related U.S. Application Data

(60) Provisional application No. 60/155,507, filed on Sep. 22, 1999.

(51) Int. Cl.[7] .................................................. A61N 5/00
(52) U.S. Cl. ............................................ 604/529; 604/3
(58) Field of Search ....................... 604/529; 600/3, 600/4

(56) References Cited

U.S. PATENT DOCUMENTS

| | | | |
|---|---|---|---|
| 3,560,291 A | 2/1971 | Foglia et al. | |
| 3,769,117 A | 10/1973 | Bowen et al. | |
| 3,974,016 A | 8/1976 | Bondybey et al. | |
| 4,069,080 A | 1/1978 | Osborne | |
| 4,156,626 A | 5/1979 | Souder | |
| 4,195,637 A | 4/1980 | Gruntzig et al. | |
| 4,251,305 A | 2/1981 | Becker et al. | |
| 4,323,071 A | 4/1982 | Simpson et al. | |
| 4,515,651 A | 5/1985 | MacLaughlin et al. | |
| 4,537,809 A | 8/1985 | Ang et al. | |
| 4,581,017 A | 4/1986 | Sahota | |
| 4,661,094 A | 4/1987 | Simpson | |
| 4,697,575 A | 10/1987 | Horowitz | |
| 4,706,652 A | 11/1987 | Horowitz | |
| 4,733,047 A | 3/1988 | Cruickshank et al. | |
| 4,744,366 A | 5/1988 | Jang | |
| 4,748,982 A | 6/1988 | Horzewski et al. | |
| 4,762,130 A | 8/1988 | Fogarty et al. | |
| 4,763,671 A | 8/1988 | Goffinet | |
| 4,771,777 A | 9/1988 | Horzewski et al. | |

(List continued on next page.)

FOREIGN PATENT DOCUMENTS

| | | |
|---|---|---|
| DE | 9102312 | 8/1992 |
| DE | 4315002 | 8/1994 |
| EP | 0633041 A1 | 1/1995 |

(List continued on next page.)

OTHER PUBLICATIONS

PCT Search Report PCT/US 99/03329 mailed Jun. 18, 1999.
–PCT Search Report PCT/US 99/03360 mailed Jun. 17, 1999.

(List continued on next page.)

*Primary Examiner*—J. Casimer Jacyna
(74) *Attorney, Agent, or Firm*—Blakely, Sokoloff, Taylor & Zafman LLP

(57) ABSTRACT

Methods and apparatuses for positioning a radiation source in vivo relative to radio-opaque markers on a catheter that delineate a therapeutic treatment length so that a therapeutic dose of radiation is delivered along the therapeutic treatment length.

12 Claims, 20 Drawing Sheets

U.S. PATENT DOCUMENTS

| | | |
|---|---|---|
| 4,771,778 A | 9/1988 | Mar |
| 4,775,371 A | 10/1988 | Mueller, Jr. |
| 4,790,315 A | 12/1988 | Mueller, Jr. et al. |
| 4,793,351 A | 12/1988 | Landman et al. |
| 4,815,449 A | 3/1989 | Horowitz |
| 4,861,520 A | 8/1989 | Van't Hooft et al. |
| 4,936,823 A | 6/1990 | Colvin et al. |
| 4,940,064 A | 7/1990 | Desai |
| 4,969,863 A | 11/1990 | Van't Hooft et al. |
| 4,976,720 A | 12/1990 | Machold et al. |
| 4,983,167 A | 1/1991 | Sahota |
| 4,994,560 A | 2/1991 | Kruper, Jr. et al. |
| 4,998,917 A | 3/1991 | Gaiser et al. |
| 5,002,560 A | 3/1991 | Machold et al. |
| 5,015,230 A | 5/1991 | Martin et al. |
| 5,019,042 A | 5/1991 | Sahota |
| 5,032,113 A | 7/1991 | Burns |
| 5,034,001 A | 7/1991 | Garrison et al. |
| 5,040,543 A | 8/1991 | Badera et al. |
| 5,046,503 A | 9/1991 | Schneiderman |
| 5,059,166 A | 10/1991 | Fischell et al. |
| 5,061,273 A | 10/1991 | Yock |
| 5,084,002 A | 1/1992 | Liprie |
| 5,087,246 A | 2/1992 | Smith |
| 5,100,429 A | 3/1992 | Sinofsky et al. |
| 5,133,956 A | 7/1992 | Garlich et al. |
| 5,137,513 A | 8/1992 | McInnes et al. |
| 5,151,149 A | 9/1992 | Swartz |
| 5,176,617 A | 1/1993 | Fischell et al. |
| 5,176,661 A | 1/1993 | Evard et al. |
| 5,180,368 A | 1/1993 | Garrison |
| 5,195,971 A | 3/1993 | Sirhan |
| 5,199,939 A | 4/1993 | Dake et al. |
| 5,213,561 A | 5/1993 | Weinstein et al. |
| 5,226,889 A | 7/1993 | Sheiban |
| 5,242,396 A | 9/1993 | Evard |
| 5,258,419 A | 11/1993 | Rolando et al. |
| 5,263,963 A | 11/1993 | Garrison et al. |
| 5,267,960 A | 12/1993 | Hayman et al. |
| 5,273,738 A | 12/1993 | Matthews et al. |
| 5,279,562 A | 1/1994 | Sirhan et al. |
| 5,282,781 A | 2/1994 | Liprie |
| 5,295,959 A | 3/1994 | Gurbel et al. |
| 5,295,960 A | 3/1994 | Aliahmad et al. |
| 5,295,995 A | 3/1994 | Kleiman |
| 5,300,281 A | 4/1994 | McMillan et al. |
| 5,302,168 A | 4/1994 | Hess |
| 5,306,246 A | 4/1994 | Sahatjian et al. |
| 5,308,356 A | 5/1994 | Blackshear, Jr. et al. |
| 5,320,824 A | 6/1994 | Brodack et al. |
| 5,334,154 A | 8/1994 | Samson et al. |
| 5,336,518 A | 8/1994 | Narayanan et al. |
| 5,350,361 A | 9/1994 | Tsukashima et al. |
| 5,352,199 A | 10/1994 | Tower |
| 5,354,257 A | 10/1994 | Roubin et al. |
| 5,380,747 A | 1/1995 | Medford et al. |
| 5,395,333 A | 3/1995 | Brill |
| 5,405,622 A | 4/1995 | Vernice et al. |
| 5,409,495 A | 4/1995 | Osborn |
| 5,411,466 A | 5/1995 | Hess |
| 5,415,664 A | 5/1995 | Pinchuk |
| 5,425,710 A | 6/1995 | Khair et al. |
| 5,441,516 A | 8/1995 | Wang et al. |
| 5,447,497 A | 9/1995 | Sogard et al. |
| 5,456,667 A | 10/1995 | Ham et al. |
| 5,458,572 A | 10/1995 | Campbell et al. |
| 5,484,384 A | 1/1996 | Fearnot |
| 5,498,227 A | 3/1996 | Mawad |
| 5,501,667 A | 3/1996 | Verduin, Jr. |
| 5,501,759 A | 3/1996 | Forman |
| 5,503,613 A | 4/1996 | Weinberger |
| 5,503,614 A | 4/1996 | Liprie |
| 5,507,301 A | 4/1996 | Wasicek et al. |
| 5,507,769 A | 4/1996 | Marin et al. |
| 5,516,336 A | 5/1996 | McInnes et al. |
| 5,540,659 A | 7/1996 | Teirstein |
| 5,542,925 A | 8/1996 | Orth |
| 5,549,552 A | 8/1996 | Peters et al. |
| 5,573,508 A | 11/1996 | Thornton |
| 5,573,509 A | 11/1996 | Thornton, Jr. |
| 5,599,306 A | 2/1997 | Klein et al. |
| 5,616,114 A | 4/1997 | Thornton et al. |
| 5,618,266 A | 4/1997 | Liprie |
| 5,643,171 A | 7/1997 | Bradshaw et al. |
| 5,645,529 A | 7/1997 | Fagan et al. |
| 5,653,691 A | 8/1997 | Rupp et al. |
| 5,658,311 A | 8/1997 | Baden |
| 5,683,345 A | 11/1997 | Waksman et al. |
| 5,688,486 A | 11/1997 | Watson et al. |
| 5,707,332 A | 1/1998 | Weinberger |
| 5,730,698 A | 3/1998 | Fischell et al. |
| 5,738,901 A | 4/1998 | Wang et al. |
| 5,762,906 A | 6/1998 | Creighton |
| 5,766,192 A | 6/1998 | Zacca |
| 5,772,642 A | 6/1998 | Ciamacco, Jr. et al. |
| 5,782,740 A | 7/1998 | Schneiderman |
| 5,782,742 A | 7/1998 | Crocker et al. |
| 5,797,869 A | 8/1998 | Martin et al. |
| 5,797,948 A | 8/1998 | Dunham |
| 5,826,588 A | 10/1998 | Forman |
| 5,836,965 A | 11/1998 | Jendersee et al. |
| 5,840,064 A | 11/1998 | Liprie |
| 5,840,067 A | 11/1998 | Berguer et al. |
| 5,851,171 A | 12/1998 | Gasson |
| 5,863,284 A | 1/1999 | Klein |
| 5,871,436 A | 2/1999 | Eury |
| 5,882,290 A | 3/1999 | Kume |
| 5,882,291 A | 3/1999 | Bradshaw |
| 5,899,882 A | 5/1999 | Waksman et al. |
| 5,910,101 A | 6/1999 | Andrews et al. |
| 5,938,582 A | 8/1999 | Ciamacco, Jr. et al. |
| 5,947,924 A | 9/1999 | Liprie |
| 5,951,458 A | 9/1999 | Hastings et al. |
| 5,954,741 A | 9/1999 | Fox |
| 5,961,765 A | 10/1999 | Kastenhofer |
| 5,964,730 A | 10/1999 | Williams et al. |
| 5,976,106 A | 11/1999 | Verin et al. |
| 5,984,963 A | 11/1999 | Ryan et al. |
| 6,117,064 A | 9/2000 | Apple et al. |
| 6,190,356 B1 | 2/2001 | Bersin |
| 6,196,996 B1 | 3/2001 | Teirstein |

FOREIGN PATENT DOCUMENTS

| | | |
|---|---|---|
| EP | 0688580 A1 | 12/1995 |
| EP | 0801961 A2 | 10/1997 |
| EP | 0829271 A2 | 3/1998 |
| EP | 0 853 957 A2 | 7/1998 |
| EP | 0865803 A2 | 9/1998 |
| EP | 0879614 A1 | 11/1998 |
| FR | 2 677 872 A1 | 12/1992 |
| WO | WO 92/17236 | 10/1992 |
| WO | WO 93/04735 | 3/1993 |
| WO | WO 94/25106 | 11/1994 |
| WO | WO 95/19807 | 7/1995 |
| WO | WO 95/26681 | 10/1995 |
| WO | WO 96/06654 | 3/1996 |
| WO | WO 96/10436 | 4/1996 |
| WO | WO 96/14898 | 5/1996 |
| WO | WO 96/19255 | 6/1996 |
| WO | WO 97/07740 | 3/1997 |
| WO | WO 97/37715 | 10/1997 |

| WO | WO 97/40889 | 11/1997 |
|---|---|---|
| WO | WO 98/01182 | 1/1998 |
| WO | WO 98/01183 | 1/1998 |
| WO | WO 98/01184 | 1/1998 |
| WO | WO 98/01185 | 1/1998 |
| WO | WO 98/39052 | 9/1998 |
| WO | WO99/15225 A1 | 4/1999 |

OTHER PUBLICATIONS

–PCT Search Report PCT/US 99/03327 mailed Jun. 18, 1999.
–PCT Search Report PCT/US 99/03343 mailed Jun. 17, 1999.
PCT Search Report PCT/US 99/03328 mailed Jun. 18, 1999.
–Vitali Verin, M.D., et al., "Intra–Arterial Beta Irradiation Prevents Neointimal Hyperplasia in a Hypercholesterolemic Rabbit Restenosis Model", Circulation, vol. 92, No. 8, pp 2284–2290, Oct. 15, 1995.
–Ron Waksman M.D. et al., "Intracoronary Radiation Before Stent Implantation Inhibits Neointima Formation in Stented Porcine Coronary Arteries", Circulation, vol. 92, No. 6, pp 1383–1386, Sep. 15, 1995.
Chrisoph Hehrlein, M.D., et al., "Low–Dose Radioactive Endovascular Stents Prevent Smooth Muscle Cell Proliferation and Neointimal Hyperplasia in Rabbits", Circulation, vol. 92, No. 6, pp 1570–1575, Sep. 15, 1995.
–Joseph G. Widermann et al., "Effects of High–Dose Intracoronary Irradiation on Vasomotor Function and Smooth Muscle Histopathology", Intracoronary Irradiation and Vasomotion, pp H125–H132, 1994.
Keith L. March, M.D. et al., "8–Methoxypsoralen and Longwave Ultraviolet Irradiation Are a Novel Antiproliferative Combination for Vascular Smooth Muscle", Circulation, vol. 87, No. 1, pp 184–191, Jan. 1993.
–Barry T. Katzen, M.D., "Mechanical Approaches to Restenosis in the Peripheral Circulation", Jan. 1996.
–Ron Waksman M.D. et al., "Intracoronary Low–Dose B–Irradiation Inhibits Neointima Formation After Coronary Artery Balloon Injury in the Swine Restenosis Model", Circulation, vol. 92, No. 10,pp 3025–3031, Nov. 15, 1995.
–Joseph G. Wiedermann, M.D. et al., "Intracoronary Irradiation Markedly Reduces Neointimal Proliferation After Balloon Angioplasty in Swine: Persistent Benefit at 6–month Follow–up", JACC vol. 25, No. 1, pp 1451–1456, May 1995.
–Dieter Liermann et al., "Prophylactic Endovascular Radiotherapy to Prevent Intimal Hyperplasia After Stent Implantation in Femoropopliteal Arteries", Cardiovascular and Interventional Radiology,vol. 17, pp 12–16, 1994.
–Roger W. Byhardt et al., "The Heart and Blood Vessels", Radiation Oncology Rationale, Technique, Results, pp 277–284, Jan. 1996.
–C.G. Soares et al., "Measurement of Radial Dose Distributions Around Small Beta Particle Emitters Using High Resolution Radiochromic Foil Dosimetry", Nuclear Technology Publishing, vol. 4, No. 1, pp 367–372, 1992.
Louis K. Wagner, PH.D et al., "Potential Biological Effects Following High X–Ray Dose Interventional Procedures", Journal of Vascular and Interventional Radiology, pp 71–84, Jan.–Feb. 1994.
–Tsunekazu Kakuta, M.D. et al., "Differences in Compensatory Vessel Enlargement, Not Intimal Formation, Account for Restenosis After Angioplasty in the Hypercholesterolemic Rabbit Model," Circulation, vol. 89, No. 6, pp 2809–2815, Jun. 1994.

–Christina Unterberg, M.D. et al., "Reduced Acute Thrombus Formation Results in Decreased Neointimal Proliferation After Coronary Angioplasty", JACC, vol. 26, No. 7, pp 1747–1754, Dec. 1995.
Lewis W. Johnson et al., "Review of Radiation Safety in the Cardiac Catheterization Laboratory", Catheterization and Cardiovascular Diagnosis, vol. 25, pp 186–194, 1992.
–Robert S. Schwartz et al., "Differential Neointimal Response to Coronary Artery Injury in Pigs and Dogs", Arteriosclerosis and Thrombosis, vol. 14, No. 3, pp 395–400, Mar. 1994.
–Michael Haude, M.D. et al, "Quantitative Analysis of Elastic Recoil after Ballon Angioplasty and After Intracoronary Implantation of Ballon–Expandable Palmaz–Schatz Stents", JACC, vol. 21, No. 1, pp 26–34, Jan. 1993.
William S. Weintraub M.D. et al., "Can Restenosis After Coronary Angioplasty Be Predicted From Clinical Variables?", JACC, vol. 21, No. 1, pp 6–14, Jan. 1993.
–Richard V. Calfee, Ph.D., "High Dose Rate Afterloader System For Endovascular Use–Neocardia", Discoveries in Radiation for Restenosis, Abstract 39, pp 119, Jan. 1996.
–Dr. Edward F. Smith III, "Issues on Handling Radioactive Devices to Prevent Restenosis", , Discoveries in Radiation for Restenosis, Abstract 40, pp 121–122, Jan. 1996.
–Richard E. Kunts, M.D. et al., "Generalized Model of Restenosis After Conventional Ballon Angioplasty, Stenting and Directional Atherectomy", JACC, vol. 21. No. 1, pp 15–25, Jan. 1993.
–Eric Van't Hooft, et al., "HDR Afterloader for Vascular Use", Discoveries in Radiation for Restenosis, Abstract 36, p 113, Jan. 1996.
–Robert E. Fischell, et al., "The Radioisotope Stent: Conception and Implementation", Discoveries in Radiation for Restenosis, Abstract 37, p 115, Jan. 1996.
–Youri Popowski M.D., et al., "Radioactive Wire in a Self–Centering Catheter System", Discoveries in Radiation for Restenosis, Abstract 38, pp 117–118, Jan. 1996.
–Philip Urban, M.D. et al., "Endovascular Irradiation with 90Y Wire", Discoveries in Radiation for Restenosis, Abstract 33, pp 103–104, Jan. 1996.
–Jose A. Condado, et al., "Late Follow–up After Percutaneous Transluminal Coronary Angioplasty (PTCA) and Intracoronary Radiation Therapy (ICRT)," Discoveries in Radiation for Restenosis, Abstract 34, p 105, Jan. 1996.
–Thomas D. Weldon, "Catheter Based Beta Radiation System", Discoveries in Radiation for Restenosis, Abstract 35, p 111, Jan. 1996.
–Ron Waksman, M.D., "Radiation in the Peripheral System at Emory," Discoveries in Radiation for Restenosis, Abstract 30, pp 93–94, Jan. 1996.
–Paul S. Teirstein et al., "Catheter–Based Radiation Therapy to Inhibit Restenosis Following Coronary Stenting," Discoveries in Radiation for Restenosis, Abstract 31, p 99, jan. 1996.
–Spencer B. King III, M.D., "Clinical Restenosis Trails Using Beta Energy Radiation," Discoveries in Radiation for Restenosis, Abstract 32, pp 101–102, Jan. 1996.
–Louis G. Martin, M.D., "Radiation for Peripheral Application: Technical Aspects, " Discoveries in Radiation for Restenosis, Abstract 27, pp 81–81, Jan. 1996.
–Alan B. Lumsden, M.D. et al, "Restenosis in Peripheral Vascular Disease," Discoveries in Radiation for Restenosis, Abstract 28, pp 83–88, Jan. 1996.

−B. Schopohl et al., "Endovascular Irradiation for Avoidance or Recurrent Stenosis After Stent Implantation in Peripheral Arteries–5 years Follow–up", *Discoveries in Radiation for Restenosis*, Abstract 29, pp 89–92, Jan. 1996.

−Joseph G. Wiedermann, M.D. et al., "Intracoronary Irradiation Markedly Reduces Restenosis After Balloon Angioplasty in a Porcine Model", *JACC*, vol. 23, No. 6, pp 1491–1498, May 1994.

−Tim A. Fischell, M.D. et al., "Low–Dose B–Particle Emission from 'Stent' Wire Results in Complete, Localized Inhibition of Smooth Muscle Cell Proliferation", *Circulation*, vol. 90, No. 6, pp 2956–2963, Dec. 1994.

Maria G. M. Hunink, M.D et al., "Risks and Benefits of Femoropopliteal Percutaneous Balloon Angioplasty", *Journal of Vascular Surgery*, vol. 17, No. 1, pp 183–194, Jan. 1993.

−Tim A. Fischell, M.D. et al., "A Beta–Particle Emitting Radioisotope Stent for The Prevention of Restenosis," *Discoveries in Radiation for Restenosis*, Abstract 23, p 65, Jan. 1996.

−Alexander N. Li et al., "A Novel Brachyehtapy Source for Treatment of Coronary Artery Restenosis," *Discoveries in Radiation for Restenosis*, Abstract 24, pp 67–72, Jan. 1996.

−Ron Waksman, M.D., "Catheter–Based Radiation In Stented Arteries", *Discoveries in Radiation for Restenosis*, Abstract 25, pp 73–74, Jan. 1996.

−Ron Waksman M.D. et al., "Endovascular Low–Dose Irradiation Inhibits Neointima Formation After Coronary Artery Balloon Injury in Swine", *Circulation*, vol. 91, No. 5, pp 1533–1539, Mar. 1, 1995.

−Z. Weshler et al., "Inhibition by Irradiation of Smooth Muscle Cell Proliferation in the De–Endothelialized Rat Aorta", *Frontiers in Radiation Biology*, pp 133–138, Oct. 1988.

−C. Hehrlein et al. "Radioactive Stents", *Discoveries in Radiation for Restenosis*, Abstract 22, pp 63–64, Jan. 1996.

−Paul Jack Hoopes, D.V.M., Ph.D. et al., "Intraoperative Irradiation of the Canine Abdominal Aorta and Vena Cava", *Int. J. Radiation Oncology Biol. Phys.*, vol. 13, pp 715–722, May 1987.

−John T. Dawson, Jr, M.D., "Theoretic Considerations Regarding Low–Dose Radiation Therapy For Prevention of Restenosis after angioplasty", *Texas Heart Institute Journal*, vol. 18, No. 1, pp 4–7, 1991.

−Robert S. Schwartz, M.D. et al. "Effect of External Beam Irradiation on Neointimal Hyperplasia After Experimental Coronary Artery Injury", *JACC*, vol. 19, No. 5, pp 1106–1113, Apr. 1992.

−Stuart Lindsay et al., "Aortic Arteriosclerosis in The Dog After Localized Aortic X–Irradiation", Circulation Research, vol. X, pp 51–60, Jan. 1962.

−Meyer Friedman et al., "The Antiatherogenic Effect of Iridium$^{192}$ Upon the Cholesterol–Fed Rabbit", Journal of Clinical Investigation, vol. 43, No. 2, pp 185–192, 1964.

PCT International Search Report for PCT Appln No. US00/21600, mailed Feb. 2, 2001 (10 pages).

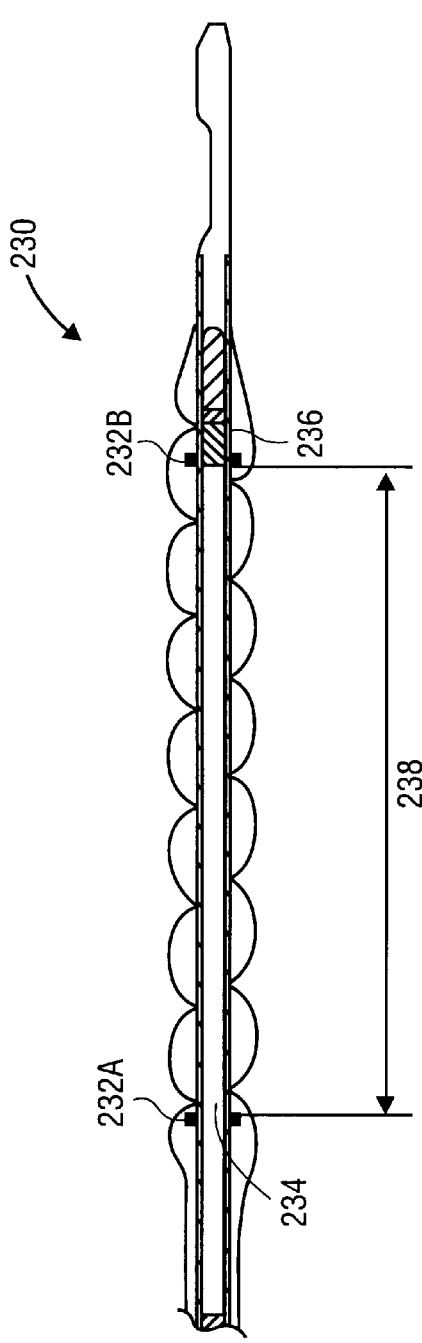
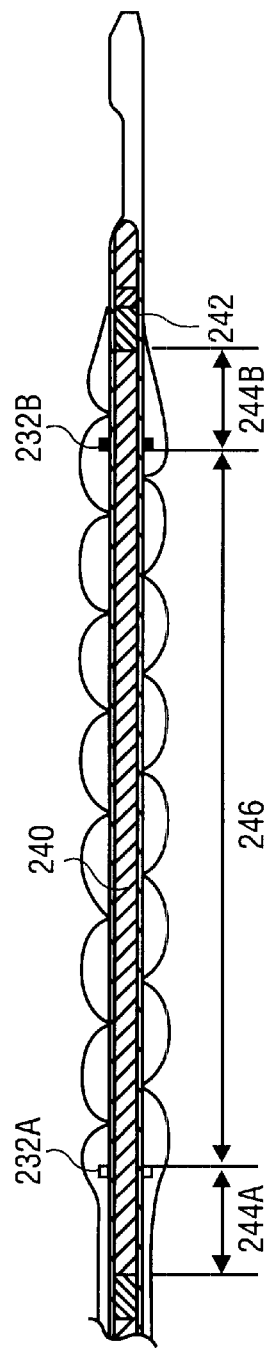
FIG. 15A
FIG. 15B

METHODS AND APPARATUSES FOR RADIATION TREATMENT

CROSS REFERENCE TO RELATED APPLICATIONS

This application claims the benefit of U.S. Provisional Application No. 60/155,507, filed Sep. 22, 1999.

FIELD OF THE INVENTION

The present invention relates to the field of intravascular radiation therapy. In particular, the present invention relates to an intravascular radiation therapy to inhibit restenosis of a vessel.

DESCRIPTION OF RELATED ART

Coronary artery balloon angioplasty is a minimally invasive technique developed as an alternative to coronary artery bypass grafting for treatment of atherosclerosis, the principle process of heart disease. There are about 450,000 coronary interventions, i.e., angioplasty, atherectomy, and stent procedures, performed annually in the U.S. However, a major limitation of this clinical procedure is the high prevalence of restenosis, or re-narrowing, of the treated vessel. Restenosis occurs approximately 30–50% of the time.

Restenosis occurs as a result of injury to the vessel wall due to the angioplasty procedure, or other procedures, such as stenting, and/or atherectomy. Restenosis is a complex process, which can involve an immediate vascular recoil, neointimal hyperplasia, and/or late vascular remodeling. Neointimal hyperplasia, a response of the body to balloon-induced physical injury of the vessel wall, is thought to be the main contributor to restenosis. Hyperplasia can result in narrowing of the vessel lumen within 3–6 months after angioplasty due to proliferation of smooth muscle cells in the region injured by the angioplasty. Restenosis can require the patient to undergo repeat angioplasty procedures or by-pass surgery with added costs and risks to the patient.

One procedure currently used to inhibit restenosis involves delivery of a prescribed dose of radiation to the injured portion of the vessel using intravascular radiation therapy (IRT). IRT procedures typically utilize radioimagery systems, such as fluoroscopy, to position a radiation source within the injured length of the vessel, for example, the dilated portion of the vessel. The radioimagery system allows a radiation source, as well as radio-opaque markers, to be viewed in vivo.

For example, once a procedure, such as an angioplasty, is completed, the physician may freeze-frame the radio-image on a viewer, such as a fluoroscope, so that anatomical landmarks may be used to subsequently position a radiation source within the dilated area. Typically, a catheter is inserted into the vessel and positioned within the dilated portion of the vessel. Catheters used in IRT commonly have an elongate, tubular shaft for receiving a radiation source that will deliver the prescribed radiation therapy. Some catheters have markers, for example, radio-opaque markers, which denote the area of the catheter in which the radioactive source will be located. The markers may be viewed using the radioimagery system to assist in positioning the catheter within vessel.

Once the catheter is positioned, a radiation source is then advanced through the lumen of the catheter shaft, and positioned within the dilated portion of the vessel. Some IRT procedures utilize a radiation source, such as radioactive seeds sealed within a source lumen, in which the source is visible on the radioimagery system, i.e., the fluoroscope. Other systems utilize radioactive sources that are not easily viewed, and, therefore, utilize markers, such as radio-opaque markers, that are visible on the radioimagery system. These markers can be used to mark one or both ends of the radiation source.

FIG. 1 illustrates a longitudinal cross-sectional view of one example of a method in the prior art for inhibiting restenosis using IRT. Following dilation of a vessel 10 using an angioplasty balloon length of 22 mm, the angioplasty balloon is removed and a catheter 12 is inserted and positioned within the dilated length. In this example, the catheter 12 may be a centering catheter designed to substantially center a radiation source 16 within the vessel 10. The catheter 12 has radio-opaque proximal and distal markers 14A and 14B that are designed to be visible using radioimagery. The markers 14A and 14B demarcate the area within which the radiation source is located to allow positioning of the catheter 12 within the vessel. The catheter 12 may be positioned using standard radioimagery techniques well known in the art in which, for example, a fluoroscope is used to observe the incremental movement of the catheter 12 until the dilated length of the vessel 10 is approximately centered between the proximal and distal markers 14A and 14B. In this example, the proximal and distal markers 14A and 14B delineate a 27 mm region to provide a 5 mm margin of error in positioning the dilated length (22 mm) within the radio-opaque markers 14A and 14B. A 27 mm radioactive source 16, such as a radioactive source wire, is then inserted and positioned within the catheter 12 so that the source end marker 18 is positioned over the distal radio-opaque marker 14B on the catheter 12. In this way the radioactive source 16 is located between the markers 14A and 14B. The radioactive source 16 is left in place until a prescribed radiation dose has been delivered to the vessel, and is then withdrawn.

A problem in current intravascular radiotherapy systems is the occurrence of an edge effect, or severe narrowing, at one or more ends of the irradiated region. A possible cause of edge effects is delivering a therapeutic dose of radiation that is too short in length to prevent restenosis throughout the treated vessel. Several factors may be responsible for not treating an adequate length of the injured vessel. Some of these have been defined as positioning errors, underestimating the length of the injury which may be longer than the dilation length due to the possibility of traumatizing segments of the vessel adjacent to the injury, and radiation dose fall-off.

Positioning of the radiation source relative to the freeze-framed image is difficult due to some movement of the vessel resulting from patient movement, blood flow, heart beats, and breathing. Thus, the radiation source may not be correctly positioned within the injured portion of the vessel, resulting in a geographical miss.

A further contributor to geographical misses, results from the projected angle of view by the radioimagery system. With radioimagery systems, such as fluoroscopy, the projected view is foreshortened so that distances appear shorter than a true perpendicular view would provide. Thus, positioning of a radiation source using a radio-image may result in the source being incorrectly positioned relative to the vessel injury.

In some cases, a minimum radiation source length may be chosen to treat a vessel injury in an attempt to prevent overdosing of non-injured lengths of vessel. If the radiation source was initially incorrectly positioned as earlier described, the selection of a minimum radiation source may result in some portions of the injured vessel left untreated.

Sometimes, during the intravascular procedures previous to the IRT, additional procedures are undertaken that cause more injury to a vessel than was anticipated. For example, if a stent does not fully deploy, the balloon used to deploy the stent may be inflated to a higher pressure, or may be moved around in an attempt to fully deploy the stent. The higher inflation pressure and movement may cause damage to the vessel in areas adjacent to the main dilated or stented length. In another example, a small blockage may be dilated outside a larger blockage in an attempt to touch-up the vessel and open it up. If this is done in several locations, often the radiation source is not positioned to treat the touched up areas. In a third example, during a balloon dilation or stenting procedure, the balloon shoulders may stretch or tear the vessel in areas adjacent to the main dilated or stented area resulting in a longer portion of the vessel being injured. When a radiation source is inserted to deliver a prescribed dose of radiation to the procedurally expected injured portions of the vessel, these additionally damaged areas may not be known and may not receive a prescribed dose of radiation.

Even if a radiation source is correctly positioned within the injured portion of a vessel, a prescribed dose of radiation may not be delivered along the entire length of the source. Some radiation sources have a dose fall-off region at the ends of the source where a lower dose of radiation is delivered than in the middle of the source. These fall-off regions vary with the particular radiation source.

FIG. 2 illustrates an example of a longitudinal dose profile of a radiation source within a centering catheter in the prior art. In one example, a therapeutic dose of radiation may be defined as at least an isodose line at 80% of a prescribed dose at 1 mm in tissue, for example, 80% of 20 Gy at 1 mm in tissue; and, a sub-therapeutic dose may be defined as a dose below an isodose line at 80% of a prescribed dose at 1 mm in tissue. It is to be understood that a therapeutic dose of radiation may be differently defined depending upon the radiation source and treatment therapy.

The dose distribution illustrates that if a 27 mm radiation source 16 is positioned correctly within the proximal and distal markers 14A and 14B, the 27 mm radiation source 16 delivers a full therapeutic dose of radiation along a length of about 22 mm with a 2–2.5 mm dose fall off at each end of the radiation source. Thus, the 27 mm radiation source 16 delivers a full therapeutic dose of radiation along a length that is shorter than the total length of the radiation source. This leaves little to no margin for treating injured lengths beyond the dilated length and does not allow room for positioning errors arising from the treatment system or physician.

Additionally, animal studies indicate that a $^{32}P$ radiation dose in the range of 5–11 Gy at 1 mm into the vessel can produce a negative, proliferative response in the vessel. This dose range may be termed a proliferative dose, and may result in restenosis, or renarrowing of the vessel, in the portions of the vessel that received the proliferative dose. As a result, vessels with maximum dilated lengths may have portions of injured tissue adjacent to each side of the dilated length which may receive a less than therapeutic dose of radiation, and may actually receive a proliferative dose of radiation, inducing edge effects.

As illustrated in the examples above, it is difficult to determine where a therapeutic dose of radiation is being delivered to an injured length of vessel. Further, it is difficult to determine if additional damage exists in the vessel, and if that additional damage is receiving a therapeutic dose of radiation, or perhaps a proliferative dose of radiation.

Thus, a need exists for a method and/or apparatus that delivers a therapeutic dose of radiation over an adequate length of a vessel to prevent restenosis following intravascular procedures such as angioplasty or stenting. Further, the method and/or apparatus should enable visualization of the length within which the therapeutic dose is delivered.

SUMMARY OF THE INVENTION

The present invention includes methods and apparatuses for positioning a radiation source in vivo relative to radio-opaque markers on a catheter that delineate a therapeutic treatment length so that a therapeutic dose of radiation is delivered along the therapeutic treatment length.

BRIEF DESCRIPTION OF THE DRAWINGS

The present invention may best be understood by referring to the following description and accompanying drawings which are used to illustrate examples of the invention. In the drawings:

FIG. 15A illustrates a longitudinal cross sectional view of one embodiment of an inactive dummy source wire positioned within a 2-marker catheter according to the present invention.

FIG. 15B illustrates a longitudinal cross sectional view of one embodiment of radioactive source wire positioned relative to the positioning of the dummy source wire within the 2-marker catheter of FIG. 15A according to the present invention.

DETAILED DESCRIPTION OF THE INVENTION

The present invention includes methods and devices for positioning a radiation source in vivo relative to radio-opaque markers on a catheter that delineate a therapeutic length, so that a therapeutic dose of radiation is delivered between the radio-opaque markers. By delivering the therapeutic dose along the therapeutic length, the present invention may help to prevent or eliminate restenosis following intravascular procedures that injure a vessel.

To effectively reduce or inhibit restenosis, it is important to deliver a therapeutic dose of radiation along an adequate length of the injured vessel. A therapeutic dose of radiation may be defined as at least the minimum amount of radiation that will effectively reduce restenosis when delivered to a prescribed location of a vessel. While it is difficult to determine the "adequate length of the injured vessel" that should receive the therapeutic dose of radiation, one embodiment of the present invention includes a method for approximating this length, called the therapeutic treatment length, and determines a total radiation source length required to deliver a therapeutic dose of radiation along the therapeutic treatment length.

Figure 1:
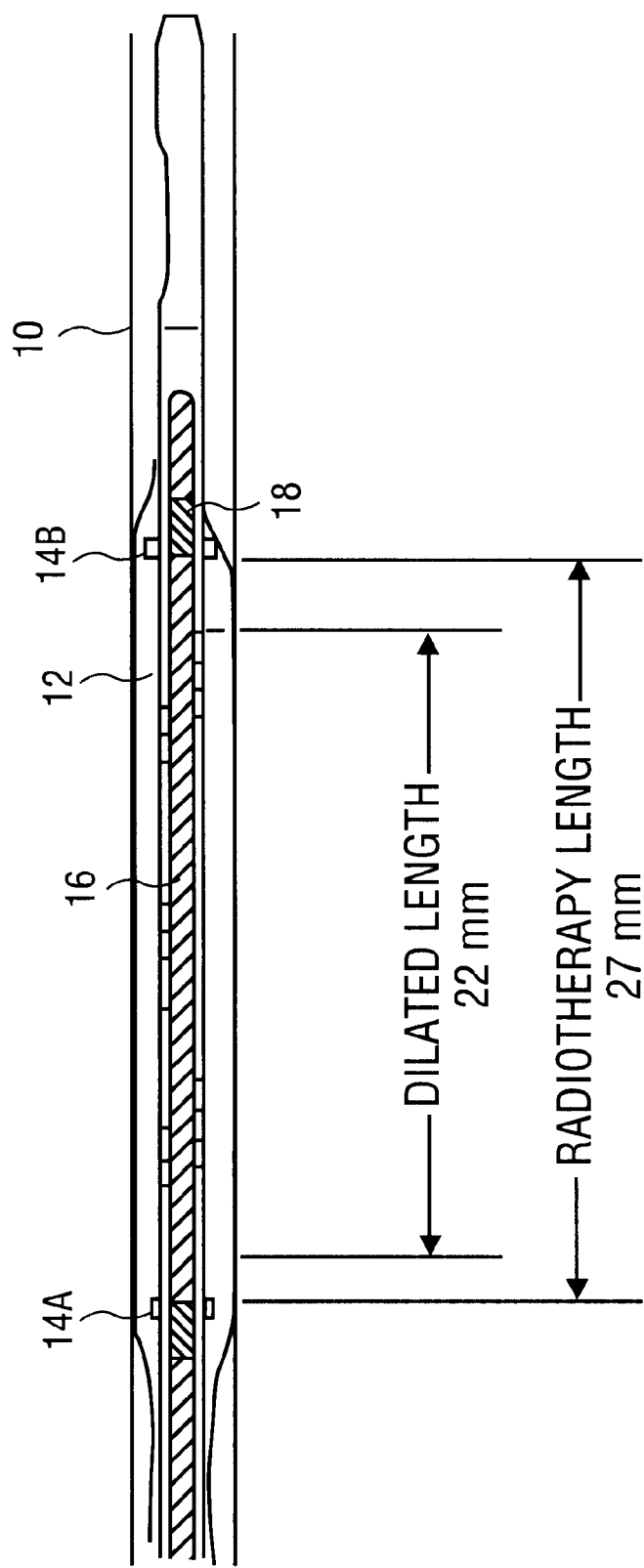
FIG. 1 illustrates a longitudinal cross-sectional view of one example of a method in the prior art for inhibiting restenosis using IRT.
Figure 2:
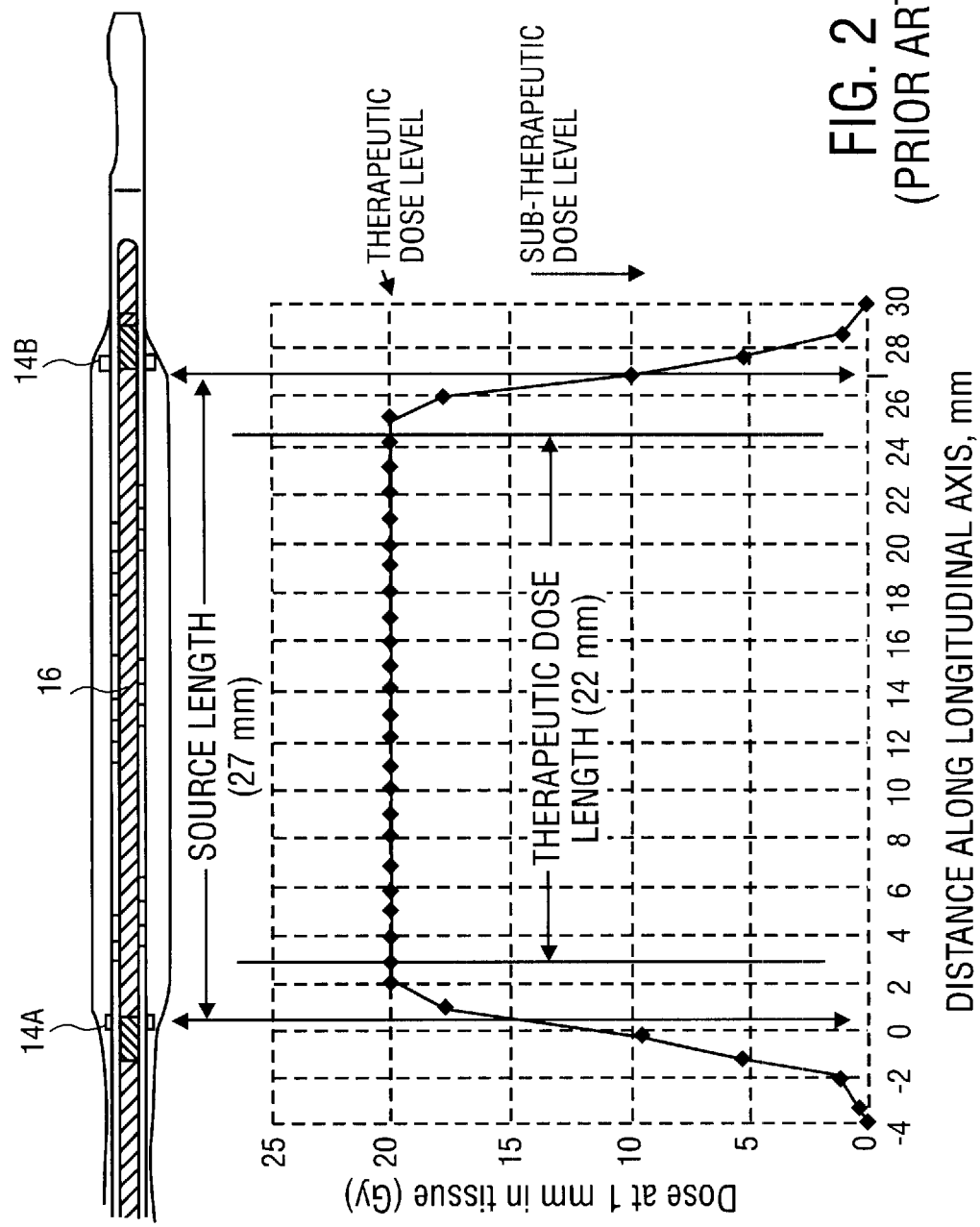
FIG. 2 illustrates an example of a longitudinal dose profile of a radiation source within a centering catheter in the prior art.
Figure 3:
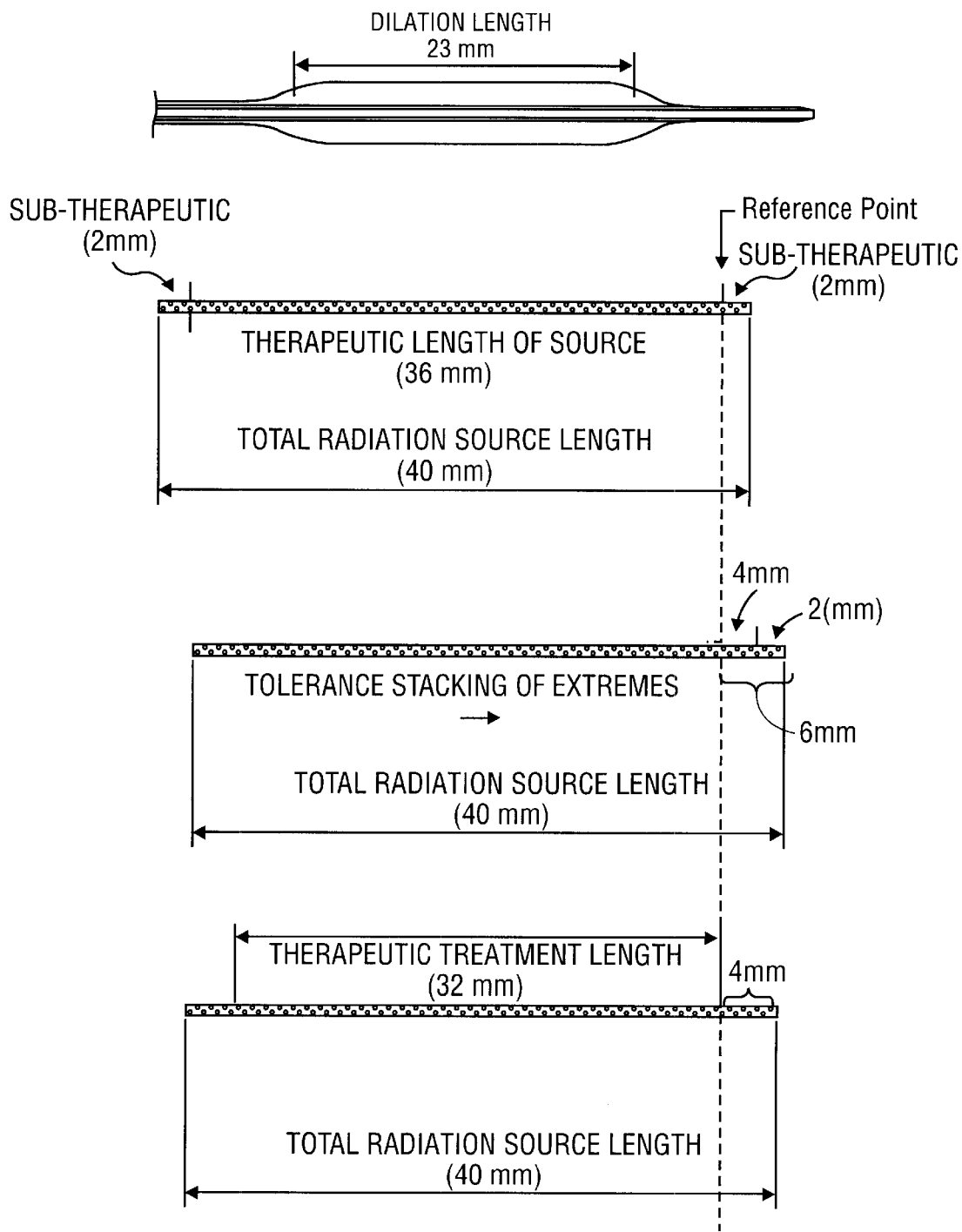
FIG. 3 illustrates a general overview of one embodiment of a method according to the present invention for developing a total radiation source length necessary to deliver a therapeutic dose of radiation over a therapeutic treatment length.

FIG. 3 illustrates a general overview of one example of one embodiment of a method for determining the total radiation source length needed deliver a therapeutic dose of radiation over a therapeutic treatment length according to the present invention. According to one embodiment of the present invention, a total radiation source length necessary to deliver a therapeutic dose of radiation over a therapeutic treatment length may be calculated as:

TOTAL RADIATION SOURCE LENGTH=DILATED LENGTH OF VESSEL+IN VIVO FACTORS LENGTH+DOSE FALL OFF LENGTH+POSITIONING TOLERANCES OF RADIATION DELIVERY SYSTEM LENGTH (IF APPLICABLE)

Although the following examples are described in regard to a vessel injured by a balloon dilation procedure, it is to be understood that the present invention may be used in treating vessels injured by procedures other than angioplasty, or balloon dilation, and that the origin of the injury to the vessel is not meant to be limiting on the present invention. For example, while the examples herein are discussed with regard to angioplasty, or dilatation procedures, the injury may arise from stenting, atherectomy, or other intravascular procedures.

In one example, a vessel may be dilated using a 23 mm angioplasty balloon resulting in an estimated maximum dilation length of 23 mm. As earlier discussed, merely positioning a radiation source over the estimated dilation length may not provide a therapeutic dose of radiation to an adequate length of vessel thus restenosis may not be prevented. Several in vivo factors may result in the radiation source being displaced from the injured length of vessel so that a longer length of vessel, i.e., longer than the 23 mm dilated length, may need to be treated with a therapeutic dose of radiation. Examples, of in vivo factors that may be considered are additional injured lengths of vessel outside the estimated dilated length, in vivo positioning errors, etc.

In dilating the vessel, there may be additional injured lengths of vessel adjacent to the dilated length due to stretching or tearing of the intima from the dilation balloon, or other device. As earlier discussed, this additional injury is difficult to determine, and thus may be estimated using experimental data, physician experience, or other sources of information.

Following the dilation, during delivery of the prescribed dose of radiation using IRT, the radiation source may be displaced relative to the injured length. These in vivo positioning errors may be due to initial catheter placement relative to the injured length, and translation of the catheter/radiation source with respect to the injured length due to movement.

As earlier discussed, error in initial catheter placement may arise from having to position the catheter in vivo by viewing the procedure using radioimagery. Translation of the catheter/radiation source with respect to the injured length may arise from movement of the beating heart, blood flow in the vessel as the heart moves, as well as some patient and vessel movement as the heart beats. These in vivo positioning errors are also difficult to determine and may be may be estimated using experimental data, physician experience, or other sources of information. In one example, the above in vivo factors may be estimated to total 11 mm.

Further, other factors related to the radiation source and the radiation delivery method should be considered in developing a requisite total radiation source length. These other factors may include the dose fall off of the particular radiation source, as well as source positioning and manufacturing tolerances associated with the radiation delivery device, if applicable.

As earlier discussed, radiation sources, and in particular, radioactive line sources, have dose fall off regions where a drop in radiation intensity occurs at the ends of the source. The rate at which the radiation intensity falls, and consequently, the length of the source that delivers a therapeutic dose to the prescribed location varies with different isotopes and source configurations. Portions of the radiation source which fall below the therapeutic dose level, may be termed the sub-therapeutic portions of the radiation source. Dose fall-off information may be obtained from radiochromic film analysis, and varies with the particular radiation source.

For example, a $^{32}$P radiation source may have dose fall off regions approximately 2 mm from each end, i.e., proximal and distal regions, where the dose is sub-therapeutic, i.e., a total of 4 mm. It is to be understood that this length is merely exemplary and that different radiation sources may have different fall-off regions depending upon the particular isotope and source configuration.

Further, radiation delivery devices, similar to most devices, have some source positioning and manufacturing tolerances particular to the fabrication and operation of the device, and the radiation source utilized by the device.

For example, the radiation delivery device may be an automated afterloader device which is described later with reference to FIG. 16. In one example, the afterloader device may utilize an inactive (or dummy) positioning source wire to determine the initial placement of an radioactive source wire relative to the catheter and then position the radioactive source wire relative to the inactive positioning wire. This inactive/radioactive positioning may result in some source positioning tolerances. Further, the radiation source positioned using the afterloader device may have source manufacturing tolerances, such as radiation source internal component shift error relating to tolerances in the fabrication of the radioactive source wire and internal components of the radioactive source wire. The source positioning and manufacturing tolerances of the afterloader device may be estimated using standard tolerance and error measurement and analysis techniques well known to those of ordinary skill in the art. In one example the source positioning and manufacturing tolerances may total 2.0 mm.

Using the above described values, a total radiation source length may then be determined by adding the initial dilated length (for example, 23 mm), a length to account for the in vivo factors (for example, 11 mm), the dose fall off length (for example, 4 mm), and, if applicable, the source positioning and manufacturing tolerances of the radiation delivery device (for example, 2 mm). Thus, the total radiation source length may be, for example, 40 mm.

Following determination of the total radiation source length, the dose fall off length is subtracted from the total radiation source length to determine the therapeutic length of source. For example, the 40 mm total radiation source length minus a total 4 mm dose fall off length results in a 36 mm therapeutic length of source with 2 mm of sub-therapeutic length at each of the proximal and distal ends of the radiation source length. If, for example, the reference point in the illustration denotes the distal end of a region within which a therapeutic dose of radiation is to be delivered, if no other sources of error or tolerances are considered, the total radiation source length would be advanced a distance 2 mm distal to the mark so that a therapeutic dose of radiation is delivered proximal to the mark.

However, if a radiation delivery system having source positioning and manufacturing tolerances is utilized, the source positioning and manufacturing tolerances may result in the location of the therapeutic length of source being displaced within a range around the reference point. For example, using the earlier discussed source positioning and manufacturing tolerances may result in the 36 mm therapeutic source length being displaced relative to the reference point +/-2 mm.

Therefore a tolerance stacking of extremes may be performed on the source positioning and manufacturing tolerances (including the dose fall off) to determine worst case positioning skews relative to the reference point. For example, using the earlier described values, a positioning skew of 6 mm distal to the reference point may be obtained. Continuing with the above example, as the distal 2 mm of the total radiation source length is sub-therapeutic due to the 2 mm dose fall off, 4 mm of the skewed length of total radiation source length contains a portion of the 36 mm therapeutic length of source. Thus, in this example, 4 mm may be subtracted from the 36 mm therapeutic length of source to obtain a 32 mm therapeutic treatment length. In positioning the total radiation source length relative to the reference point, the distal end of the total radiation source may be positioned a distance 4 mm distal to the reference point so that therapeutic dose of radiation is delivered proximal of the reference point. In this way the distal end of the radiation source is extended past the reference point a distance which includes positioning tolerances.

Thus, according to one embodiment of a method of the present invention, the total radiation source length may be approximated as the minimum radiation source length that may be used to deliver a therapeutic dose of radiation along the therapeutic treatment length.

It is to be noted that in one embodiment, the positioning tolerances may be determined by stacking the extreme tolerances, however, other methods of error and tolerance analysis may also be used to arrive at a total radiation source length which delivers a therapeutic dose of radiation to the therapeutic treatment length in accordance with the teachings of the present invention. Additionally, it is to be understood that other sources of error and tolerances may also be incorporated into the design of the total radiation source length.

Further, while one exemplary total radiation source length is described, it is to be understood that various total radiation source lengths may be obtained for use with various dilation length indications. This applies to solid line sources, as well as seed sources, which may be arranged in a line configuration by using multiple seeds, pellets with ribbon sources, and source wires.

Also, smaller length radiation sources with multi-functional capability may be used to achieve an effective total radiation source length through the use of stepping protocols. Radiation sources, for example, radiation source wires, are expensive to produce, and have a time limited efficacy due to radioactive decay. Thus, radiation sources are usually manufactured in only a few industry standard lengths. For example, there are currently over twelve different stent plus balloon dilation lengths ranging from 16 mm to 44 mm. Requiring a different single radiation source length to accommodate each of the specific lengths, could entail substantial expense for use in treating only a fraction of the patients. Thus, in this and the following embodiments, although a single total radiation source length is discussed and illustrated, it is to be understood that a single radiation source, smaller than the total radiation source length, may be used according to a stepping protocol so that a therapeutic dose of radiation is delivered along the therapeutic treatment length. This allows the single, smaller radiation source to be used in treating therapeutic treatment length of differing lengths.

The following figures illustrate several embodiments of methods and apparatuses according to the present invention that provide delivery of a therapeutic dose of radiation along a therapeutic treatment length utilizing the method discussed in reference to FIG. 3. The following figures provide for visualization of the therapeutic treatment length along which a therapeutic dose of radiation is delivered using radio-opaque markers.

2-MARKER CATHETER

Figure 4:
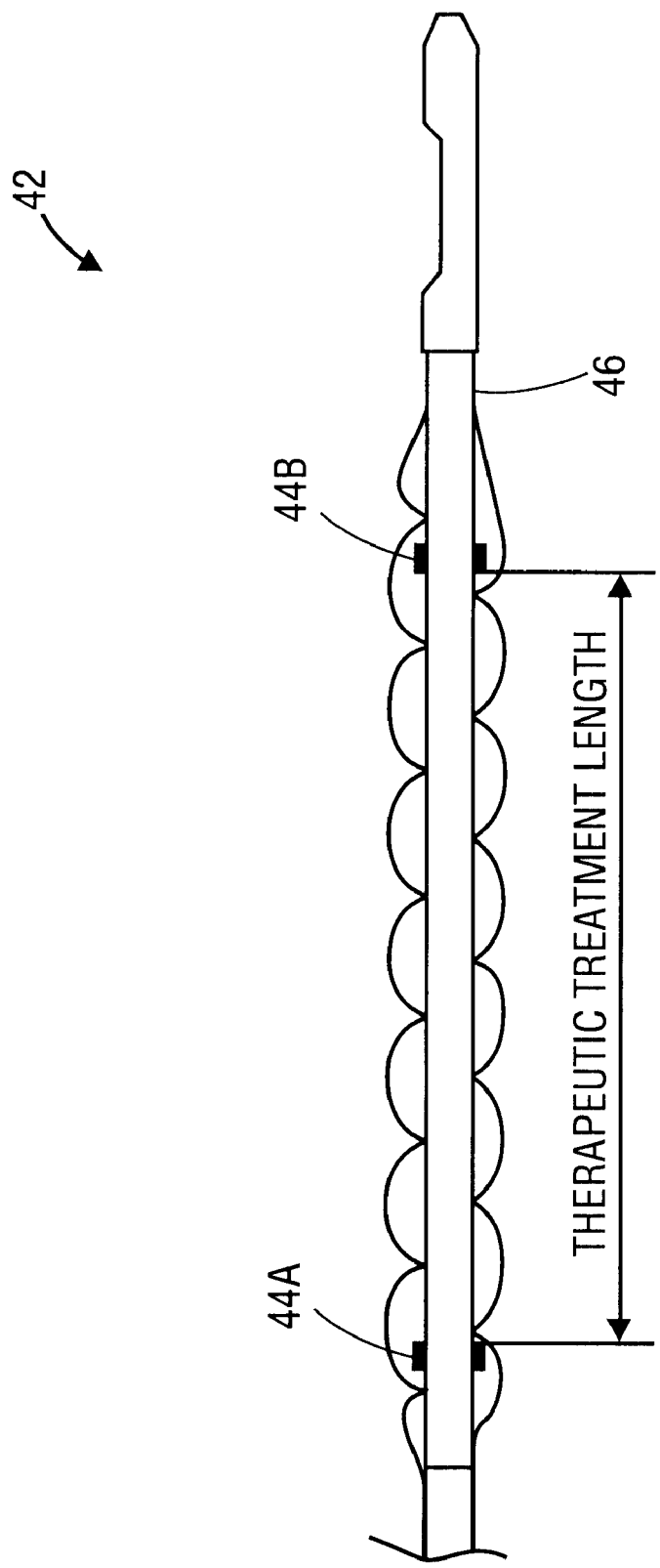
FIG. 4 illustrates a longitudinal cross-sectional view of one embodiment of a 2-marker catheter according to the present invention.

FIG. 4 illustrates a longitudinal cross-sectional view of one embodiment of a 2-marker catheter according to the present invention. As earlier discussed, positioning of a radiation source relative to an injury can be difficult due to various sources of error and tolerances. To aid in correct placement of the catheter relative to the injury, a method for denoting the location of the therapeutic treatment length is beneficial. By clearly indicating the therapeutic treatment length, the potential for positioning errors and geographical misses is reduced as it is easier to position the dilated portion of the vessel within the therapeutic treatment length. Thus, according to one embodiment of the present invention, radio-opaque proximal and distal catheter markers are located on a catheter to define a therapeutic treatment length, or therapeutic treatment length, in between, so that a radiation source may be positioned relative to the markers to allow delivery of a therapeutic dose of radiation along the therapeutic treatment length.

In the embodiment illustrated in FIG. 4, the catheter 42 has radio-opaque proximal and distal markers 44A and 44B located on the catheter shaft 46. The shaft 46 is an elongate, tubular structure that has a lumen for receiving a radiation source, not shown. The catheter 42 may be either open or closed ended and may have other structures for accepting a guidewire or support wire. The markers 44A and 44B are spaced apart so as to define a therapeutic treatment length, measured as the distance between markers 44A and 44B. In one embodiment, the therapeutic treatment length may be determined as earlier described with reference to FIG. 3. In one embodiment, the therapeutic treatment length may be measured as the distance between the distal edge of the proximal marker 44A and the proximal edge of the distal marker 44B. The therapeutic length denotes the region where the radiation source will deliver a therapeutic dose of radiation when correctly positioned relative to the markers 44A and 44B. Lengths of the vessel outside the markers 44A and 44B may receive a sub-therapeutic dose. It is to be noted that the lumen of the shaft 42 is of a length that can receive the total radiation source length when correctly positioned so that a therapeutic dose of radiation is delivered along the therapeutic treatment length.

In one embodiment, the catheter 42 may be a centering catheter, such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21. In this embodiment, the catheter markers 44A and 44B delineate the therapeutic treatment length, as well as the length within which the therapeutic treatment length is radially centered. Centering the therapeutic portion of the radioactive source inside the vessel ensures that an approximately uniform therapeutic dose is delivered radially as well as axially to the vessel. Offsetting the sub-therapeutic portions of the radioactive source mitigates overdosing of the vessel wall. It is to be understood that other centering catheters, as well as other non-centering catheters, may also be used.

In one embodiment, the catheter 42 may be positioned in a vessel lumen using radioimagery so that the dilated length of vessel is substantially longitudinally centered between the proximal and distal catheter markers 44A and 44B. It is to be understood that while the markers and imaging systems are described in this and the following figures with reference to radioimagery, such as fluoroscopy, and markers, such as radio-opaque markers, that can be viewed using radioimagery, other markers and imaging systems may also be used. It is to be understood that the length of the catheter 42 and the therapeutic treatment length denoted by the proximal and distal catheter markers 44A and 44B are chosen based upon the initial dilated length of the treated site and such other factors as those earlier discussed in regard to FIG. 3.

In one example, the catheter 42 may coupled to a radiation delivery device, such as an afterloader device, with a key connector that provides the afterloader device with information regarding the particular catheter, i.e., diameter, length, therapeutic length, and marker locations. This information may allow the afterloader device to determine the positioning of a radiation source relative to the catheter markers 44A and 44B, so that a therapeutic dose is delivered along the therapeutic treatment length. It is to be understood that the catheter 42 is not required to be used with an automated afterloader device or key connector, and that a manual radiation delivery device or other automated (including semi-automated) radiation delivery device may be used.

Once the therapeutic treatment length delineated by the markers 44A and 44B has been positioned within the vessel, the markers 44A and 44B may be used for positioning a radiation source inside the catheter so that a therapeutic dose of radiation is delivered along the therapeutic treatment length. In this way, the present invention visually demarcates the length along which a therapeutic dose of radiation is delivered to a vessel. This is contrast to prior art methods of delivering IRT which did not clearly demarcate the area in which a therapeutic dose of radiation is delivered. Positioning a radiation source relative to the markers 44A and 44B so that a therapeutic dose of radiation is delivered along the therapeutic treatment length may be accomplished by several means as described in the several embodiments of the present invention that follow.

3-MARKER CATHETER

Figure 5:
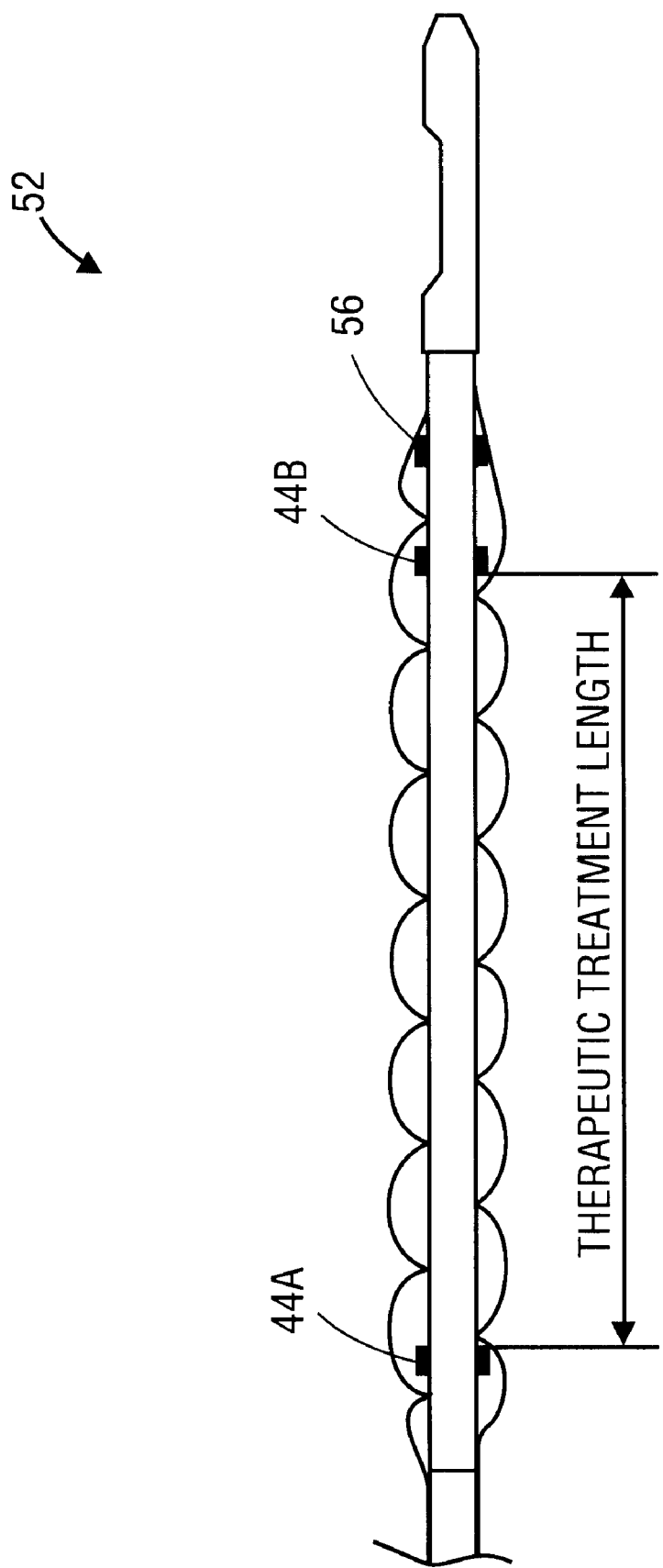
FIG. 5 illustrates a longitudinal cross-sectional view of one embodiment of a 3-marker catheter according to the present invention.

FIG. 5 illustrates a longitudinal cross-sectional view of one embodiment of a 3-marker catheter according to the present invention. In the embodiment illustrated in FIG. 5, the catheter 52 has a radio-opaque proximal and distal markers 44A and 44B that delineate a therapeutic treatment length and an additional third marker, a source positioning marker 56. In one embodiment, the catheter 52 maybe a centering catheter, such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21. The source positioning marker 56 is located a distance distal to marker 44B and is used in positioning a radiation source relative to markers 44A and 44B so that a therapeutic dose of radiation is delivered along the therapeutic treatment length. In one embodiment, the distance is equal to at least the distal length of the sub-therapeutic portion of the radiation source to be inserted, and may further include a length for positioning tolerances as earlier described in reference to FIG. 3. In this way depending upon the radiation source and radiation source delivery device, the distal end of the radiation source may be advanced to the source positioning marker 56 to allow a therapeutic dose of radiation to be delivered along the therapeutic treatment length.

Alternatively, the source positioning marker 52 may be located instead a distance proximal to the proximal marker 44A. In one embodiment, the distance is equal to at least the proximal length of the sub-therapeutic portion of the radiation source to be inserted, and may further include a length for positioning tolerances as earlier described in reference to FIG. 3. In this alternative embodiment, the proximal end of the radiation source would be advanced to the source positioning marker 56 to allow a therapeutic dose of radiation to be delivered along the therapeutic treatment length.

2-MARKER CATHETER, ELONGATED MARKER

Figure 6:
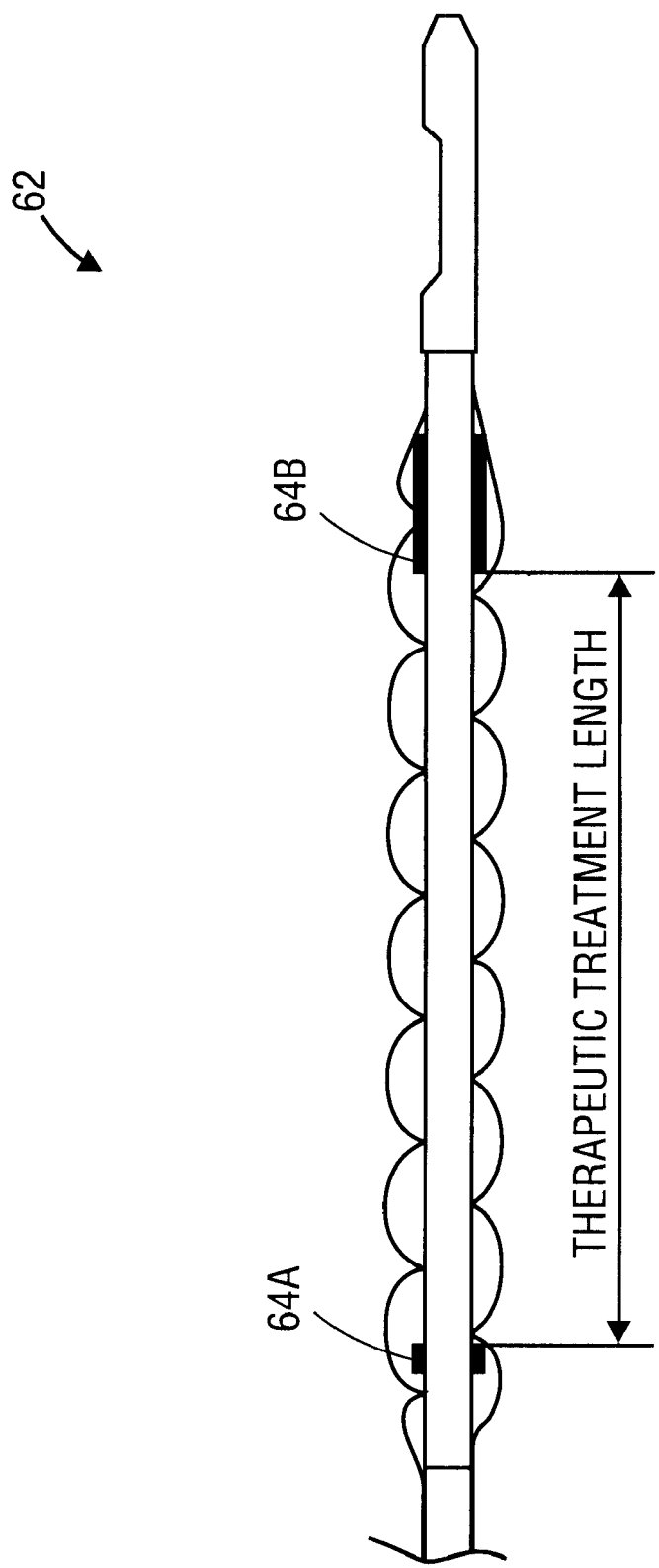
FIG. 6 illustrates a longitudinal cross-sectional view of one embodiment of a 2-marker catheter having an elongated marker according to the present invention.

FIG. 6 illustrates a longitudinal cross-sectional view of one embodiment of a 2-marker catheter having an elongated marker according to the present invention. In the embodiment illustrated in FIG. 6, the catheter 62 has a radio-opaque proximal and distal markers 64A and 64B that delineate a therapeutic treatment length as earlier described in reference to FIG. 3 and FIG. 4. In one embodiment, the catheter 62 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21. In this embodiment, the marker 64B is distally elongated a distance outside the therapeutic treatment length and is used in positioning a radiation source so that a therapeutic dose of radiation is delivered along the therapeutic treatment length. In one embodiment, the elongated distance is equal to at least the distal length of the sub-therapeutic portion of the radiation source to be inserted, and may further include a length for positioning tolerances as earlier described in reference to FIG. 3. In this way depending upon the radiation source and radiation source delivery device, the distal end of the radiation source may be advanced until it just exits the distal side of the elongated marker 64B, so that a therapeutic dose of radiation is delivered along the therapeutic treatment length.

Alternatively, the proximal marker 64A may be proximally elongated a distance outside the therapeutic treatment length. In one embodiment, the elongated distance is equal to at least the proximal length of the sub-therapeutic portion of the radiation source to be inserted, and may further include a length for positioning tolerances as earlier described in reference to FIG. 3. In this alternative embodiment, the proximal end of the radiation source may be advanced until the proximal end of the radiation source just passes inside the proximal edge of the elongated proximal marker 64A, so that a therapeutic dose of radiation is delivered along the therapeutic treatment length.

2-MARKER CATHETER WITH A DEAD END LUMEN

Figure 7:
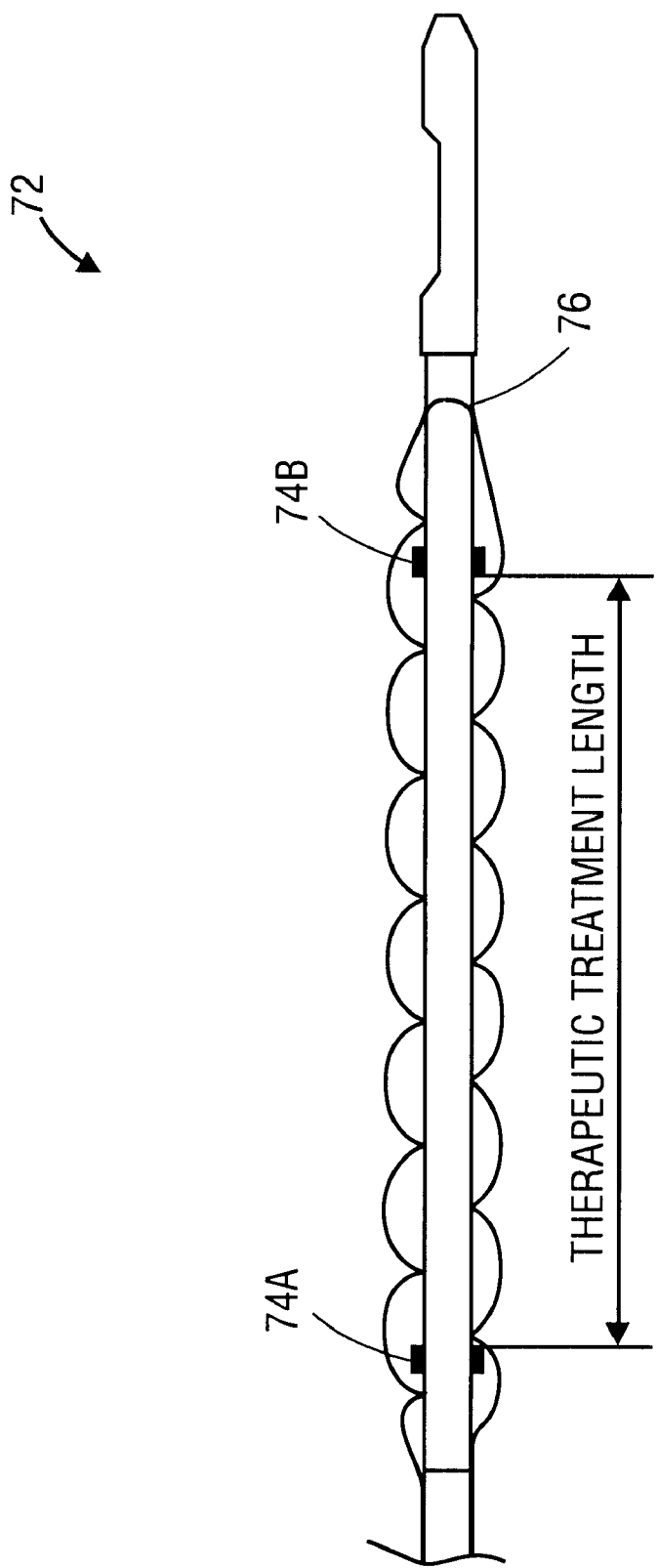
FIG. 7 illustrates a longitudinal cross-sectional view of one embodiment of a 2-marker catheter with a dead end lumen according to the present invention.

FIG. 7 illustrates a longitudinal cross-sectional view of one embodiment of a 2-marker catheter with a dead end lumen according to the present invention. In the embodiment illustrated in FIG. 7, the catheter 72 has a radio-opaque proximal and distal markers 74A and 74B that delineate a therapeutic treatment length and a dead end lumen 76. In one embodiment, the catheter 72 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21. The dead end lumen 76 terminates at a distance distal to marker 74B and is used in positioning a radiation source relative to markers 74A and 74B so that a therapeutic dose of radiation is delivered along the therapeutic treatment length. In one embodiment, the dead end lumen 76 is located a distance equal to at least the distal sub-therapeutic region of the radiation source to be inserted, and may further include a length defined by one or more of the positioning earlier described in reference to FIG. 3. In this way, depending upon the radiation source and radiation source delivery device, the distal end of the radiation source may be advanced until it stops at the dead end lumen 76 so that a therapeutic dose of radiation to be delivered along the therapeutic treatment length.

1-MARKER RADIATION SOURCE

Figure 8:
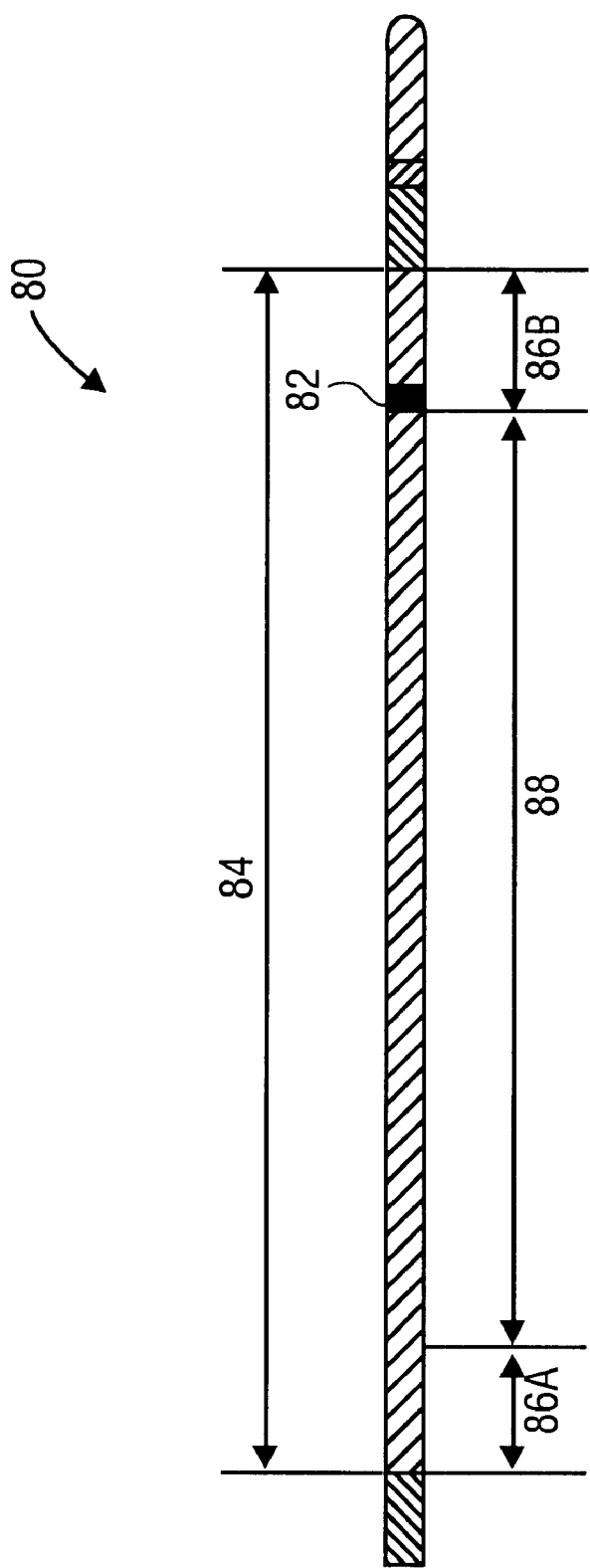
FIG. 8 illustrates an external side view of one embodiment of a radiation source having a marker according to the present invention.

FIG. 8 illustrates an external side view of one embodiment of a radiation source having a marker according to the present invention. In the embodiment illustrated in FIG. 8, the radiation source 80 has a radio-opaque marker 82 that located within the radioactive region 84 of said radiation source 80. The marker 82 may be used in positioning the radiation source 80 relative to markers 44A and 44B illustrated with reference to FIG. 4 so that a therapeutic dose of radiation is delivered along the therapeutic treatment length. In one embodiment, the radiation region 84 may further have a therapeutic dose region 88 and proximal and distal sub-therapeutic dose regions 86A and 86B located at each end of the therapeutic dose region 88. In one embodiment the marker 82 may be located at a distance proximal to the distal end of the radiation source 80 where the distance is at least the length of the distal sub-therapeutic dose region 86B. This distance may further include a length define by one or more positioning tolerances as discussed in reference to FIG. 3. In this way depending upon the radiation source and radiation source delivery device, the marker 82 may be aligned with a marker such as the marker 44B in FIG. 4, so that a therapeutic dose of radiation may be delivered along the therapeutic treatment length.

Alternatively, the marker 82 may be located instead a distance distal to the proximal end of the radiation source 80 where the distance is at least equal to the length of the proximal sub-therapeutic dose region 86A, and may further include a length define by one or more positioning tolerances as discussed in reference to FIG. 3. In this way depending upon the radiation source and radiation source delivery device, the marker 82 may be aligned with a marker such as the marker 44A in FIG. 4, so that a therapeutic dose of radiation may be delivered along the therapeutic treatment length.

2-MARKER RADIATION SOURCE

Figure 9:
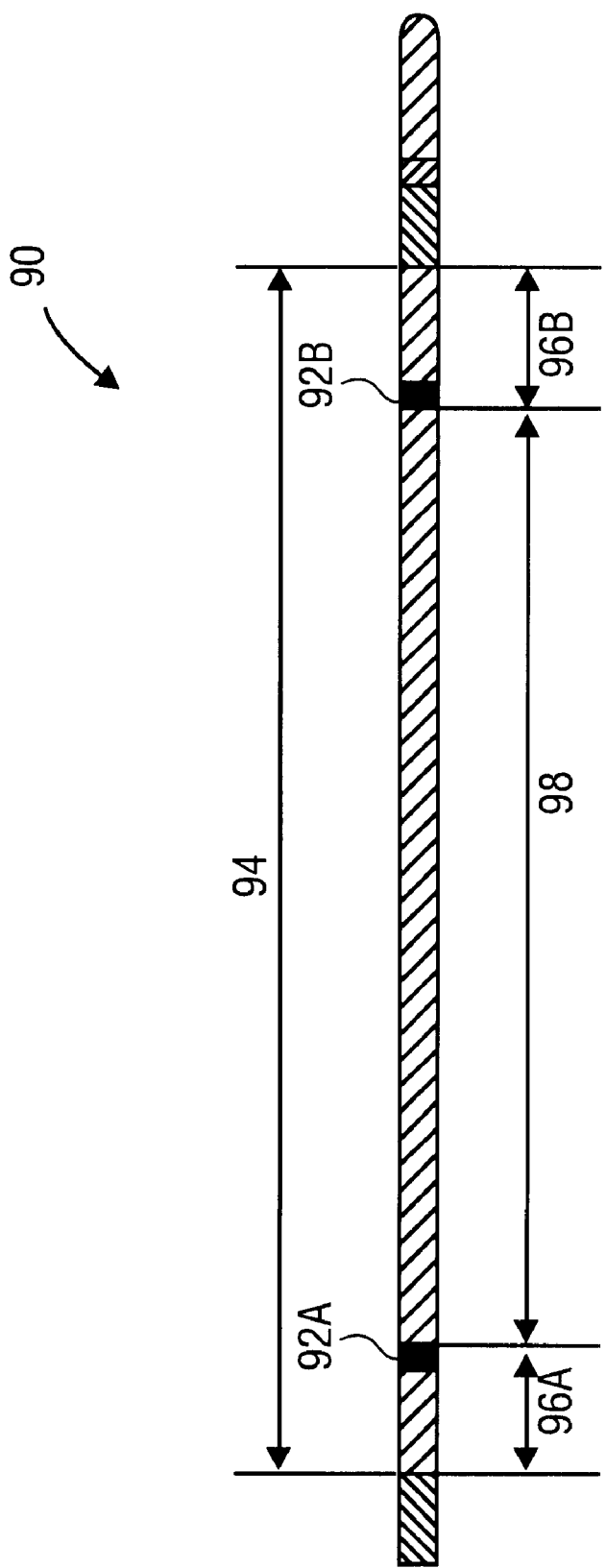
FIG. 9 illustrates an external side view of one embodiment of a 2-marker radiation source according to the present invention.

FIG. 9 illustrates an external side view of one embodiment of a 2-marker radiation source according to the present invention. In the embodiment illustrated in FIG. 9, the radiation source 90 has proximal and distal radio-opaque markers 92A and 92B that are located within the radioactive region 94 of said radiation source 90. The markers 92A and 92B may be used in positioning the radiation source 90 within a catheter so that a therapeutic dose of radiation is delivered between the markers 92A and 92B. In one embodiment, the radiation source 90 may be used in conjunction with a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21. In one embodiment, the radiation region 94 may further have a therapeutic dose region 98 and proximal and distal sub-therapeutic dose regions 96A and 96B located at each end of the therapeutic dose region 98. In one embodiment, the markers 92A and 92B may be spaced apart so as to define the therapeutic dose region 98 of the radiation source 90.

RADIATION DELIVERY SYSTEM INCLUDING A 2-MARKER CATHETER AND A RADIOACTIVE SOURCE

Figure 10:
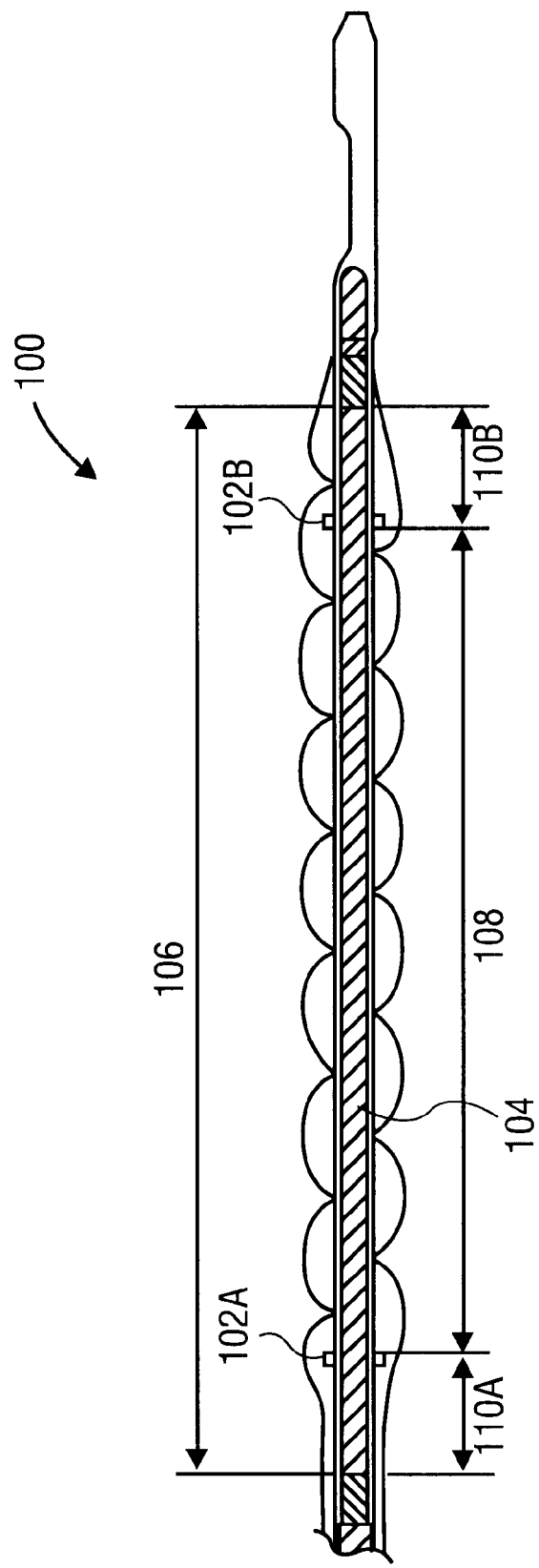
FIG. 10 illustrates a longitudinal cross-sectional view of one embodiment of a radiation delivery system which includes a 2-marker catheter used in conjunction with a radiation source according to the present invention.

FIG. 10 illustrates a longitudinal cross-sectional view of one embodiment of a radiation delivery system which includes a 2-marker catheter used in conjunction with a radiation source according to the present invention. In one embodiment, the catheter 100 is used in conjunction with a radiation source 104 so that a therapeutic dose of radiation is delivered between the proximal and distal radio-opaque markers 102A and 102B. In one embodiment, the catheter 100 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21.

In one embodiment, the radiation source 104 may have radioactive region 106 which includes a therapeutic dose region 108 and proximal and distal sub-therapeutic dose regions 110A and 110B. In one embodiment, the markers 102A and 102B may be spaced apart along the catheter 100 at a distance less than or equal to the therapeutic dose region 108 of the radiation source 106. In another embodiment, the markers 102A and 102B may be spaced apart along the catheter 100 at a distance less than or equal to the therapeutic dose region 108 minus a distance for positioning tolerances as earlier discussed in reference to FIG. 3. To accommodate the sub-therapeutic dose regions 110A and 110B, the lumen of the catheter 100 extends a distance proximal and distal to the markers 102A and 102B, each distance being at least equal to the respective sub-therapeutic dose regions 110A and 110B, and may include an additional length for positioning tolerances as discussed with reference to FIG. 3. In this way, a therapeutic dose of radiation is delivered between the markers 102A and 102B.

RADIATION DELIVERY SYSTEM INCLUDING A 2-MARKER CATHETER WITH DEAD END LUMEN AND A RADIOACTIVE SOURCE

Figure 11:
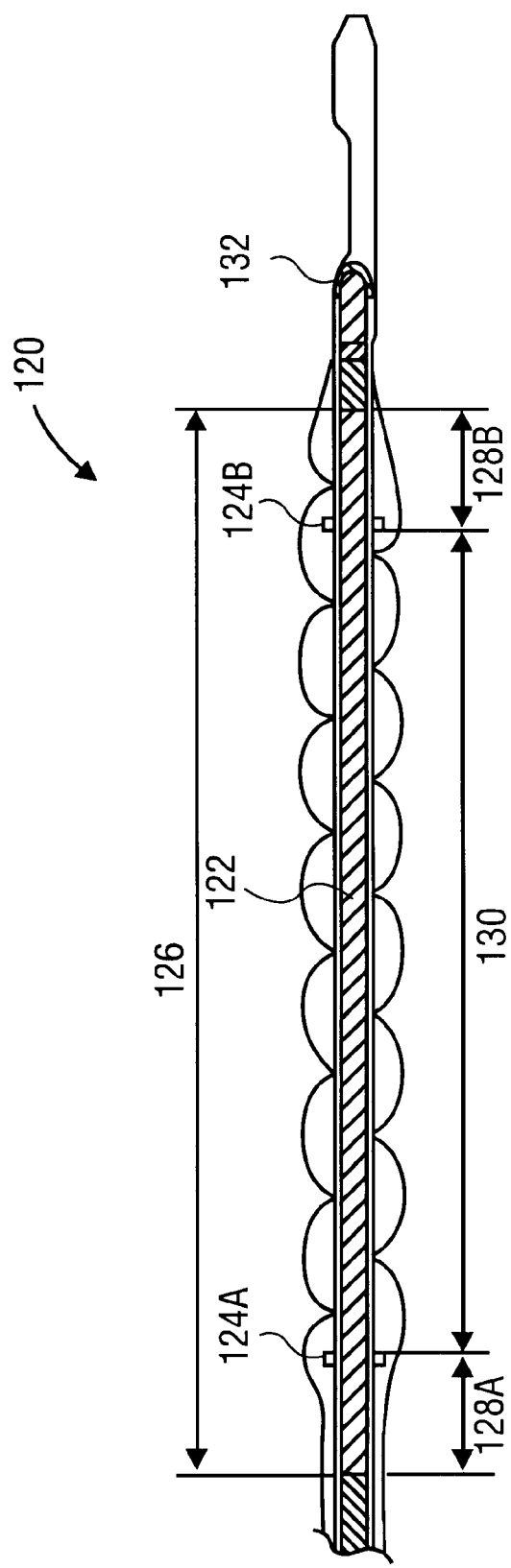
FIG. 11 illustrates a longitudinal cross-sectional view of one embodiment of a radiation delivery system which includes a 2-marker catheter with dead end lumen used in conjunction with a radiation source according to the present invention.

FIG. 11 illustrates a longitudinal cross-sectional view of one embodiment of a radiation delivery system which includes a 2-marker catheter with dead end lumen used in conjunction with a radiation source according to the present invention. In this embodiment, the catheter 120 is used in conjunction with a radiation source 122 so that a therapeutic dose of radiation is delivered between the first and second radio-opaque markers 124A and 124B. In one embodiment, the catheter 120 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21.

In one embodiment, the radiation source 122 may have a radioactive region 126 which includes proximal and distal sub-therapeutic dose regions 128A and 128B and a therapeutic dose region 130 located in between. Marker 124B may be located a distance proximal to the dead end lumen 132. In one embodiment, this distance is equal to at least the length of the distal sub-therapeutic dose region 128B of the radiation source 122, and may also further include a positioning tolerance length as discussed in reference to FIG. 3. Marker 124A is located a distance proximal to marker 124B equal to the therapeutic dose region 130 of the radiation source 122.

RADIATION DELIVERY SYSTEM INCLUDING A 2-MARKER CATHETER AND A RADIATION SOURCE HAVING A MARKER

Figure 12:
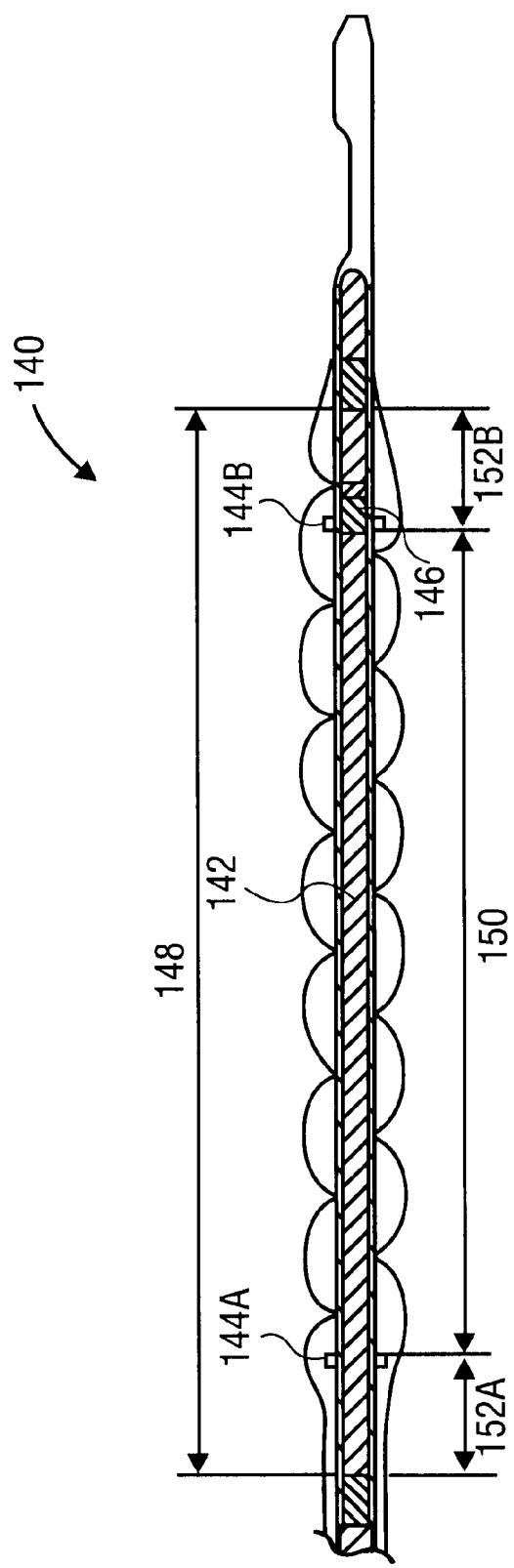
FIG. 12 illustrates a longitudinal cross-sectional view of one embodiment of a radiation delivery system which includes a 2-marker catheter used in conjunction with a radiation source having a marker according to the present invention.

FIG. 12 illustrates a longitudinal cross-sectional view of one embodiment of a radiation delivery system which includes a 2-marker catheter used in conjunction with a radiation source having a marker according to the present invention. In this embodiment, the catheter 140 is used in conjunction with a radiation source 142 having a first marker 146 so that a therapeutic dose of radiation is delivered between the second and third radio-opaque markers 144A and 144B. In one embodiment, the catheter 140 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21.

In one embodiment, the radiation source 142 may have radioactive region 148 which includes a therapeutic dose region 150 and proximal and distal sub-therapeutic dose regions 152A and 152B. In one embodiment, the first marker 146 is located a distance proximal to the distal end the radiation source 142 that is equal to at least the length of the distal sub-therapeutic dose region 152B. The distance may also further include a positioning tolerance length as discussed in reference to FIG. 3. Markers 144A and 144B are spaced apart along the catheter 140 at a distance less than or equal to the therapeutic dose region 150 of the radiation source 142. In this way the marker 146 is advanced within the catheter 140 until the marker 146 is substantially aligned with the distal marker 144B so that a therapeutic dose of radiation is delivered between the markers 144A and 144B.

In another embodiment, the radiation source 142 may have the marker 146 located a distance distal to the proximal end of the radiation source 142. In one embodiment, the distance may be equal to at least the length of the proximal sub-therapeutic dose region 152A. The distance may also further include a positioning tolerance length. In this way the marker 146 is advanced within the catheter 140 until the marker 146 is substantially aligned with the proximal marker 144A so that a therapeutic dose of radiation is delivered between the markers 144A and 144B.

RADIATION DELIVERY SYSTEM INCLUDING A 2-MARKER CATHETER HAVING AN ELONGATED MARKER AND A RADIATION SOURCE

Figure 13:
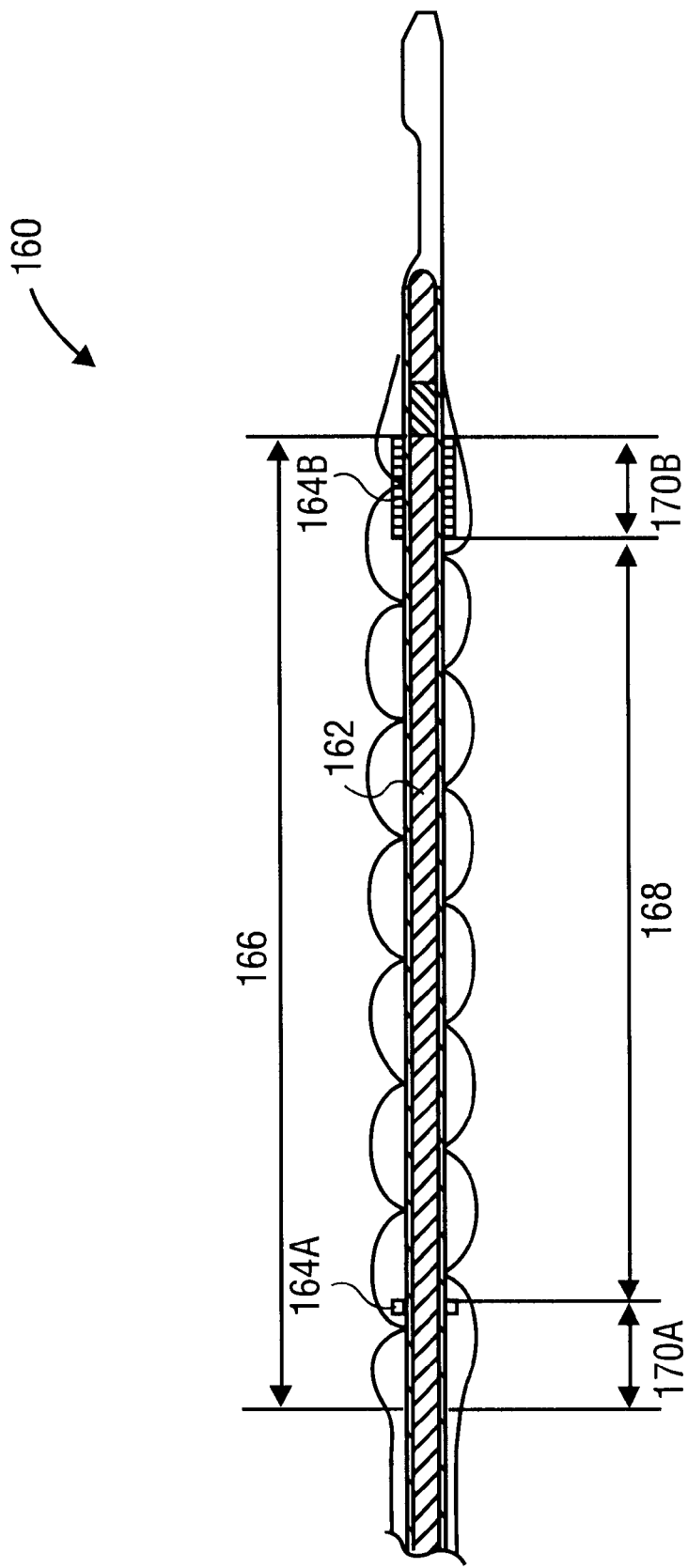
FIG. 13 illustrates a longitudinal cross-sectional view of one embodiment of a radiation delivery system which includes a 2-marker catheter having an elongated marker used in conjunction with a radiation source according to the present invention.

FIG. 13 illustrates a longitudinal cross-sectional view of one embodiment of a radiation delivery system which includes a 2-marker catheter having an elongated marker used in conjunction with a radiation source according to the present invention. In this embodiment, the catheter 160 is used in conjunction with a radiation source 162 so that a therapeutic dose of radiation is delivered between the proximal and distal radio-opaque markers 164A and 164B. In one embodiment, the catheter 160 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21.

In one embodiment, the radiation source 162 may have radioactive region 166 which includes a therapeutic dose region 168 and proximal and distal sub-therapeutic dose regions 170A and 170B. In one embodiment, the proximal and distal markers 164A and 164B are spaced a distance apart so as to define a therapeutic treatment length. In one embodiment, the distal marker 164B is distally elongated outside the therapeutic treatment length a distance equal to at least the length of the distal sub-therapeutic dose region 170B. The distance may also further include a length for positioning tolerances as discussed in reference to FIG. 3. The radiation source 162 may be positioned within the catheter 160 so that the distal end of the radioactive region 166 just exits the distal end of the distal elongated marker 164B. In this way a therapeutic dose of radiation is delivered along the therapeutic treatment length between markers 164A and 164B.

In another embodiment, the proximal marker 164A is proximally elongated outside the therapeutic treatment length a distance equal to at least the length of the proximal sub-therapeutic dose region 170A. The distance may also further include a length for positioning tolerances. The radiation source 162 may be positioned within the catheter 160 so that the proximal end of the radioactive region 166 just enters the proximal end of the elongated proximal marker 164A. In this way a therapeutic dose of radiation is delivered along the therapeutic treatment length.

RADIATION DELIVERY SYSTEM INCLUDING A 3-MARKER CATHETER AND A RADIATION SOURCE

Figure 14:
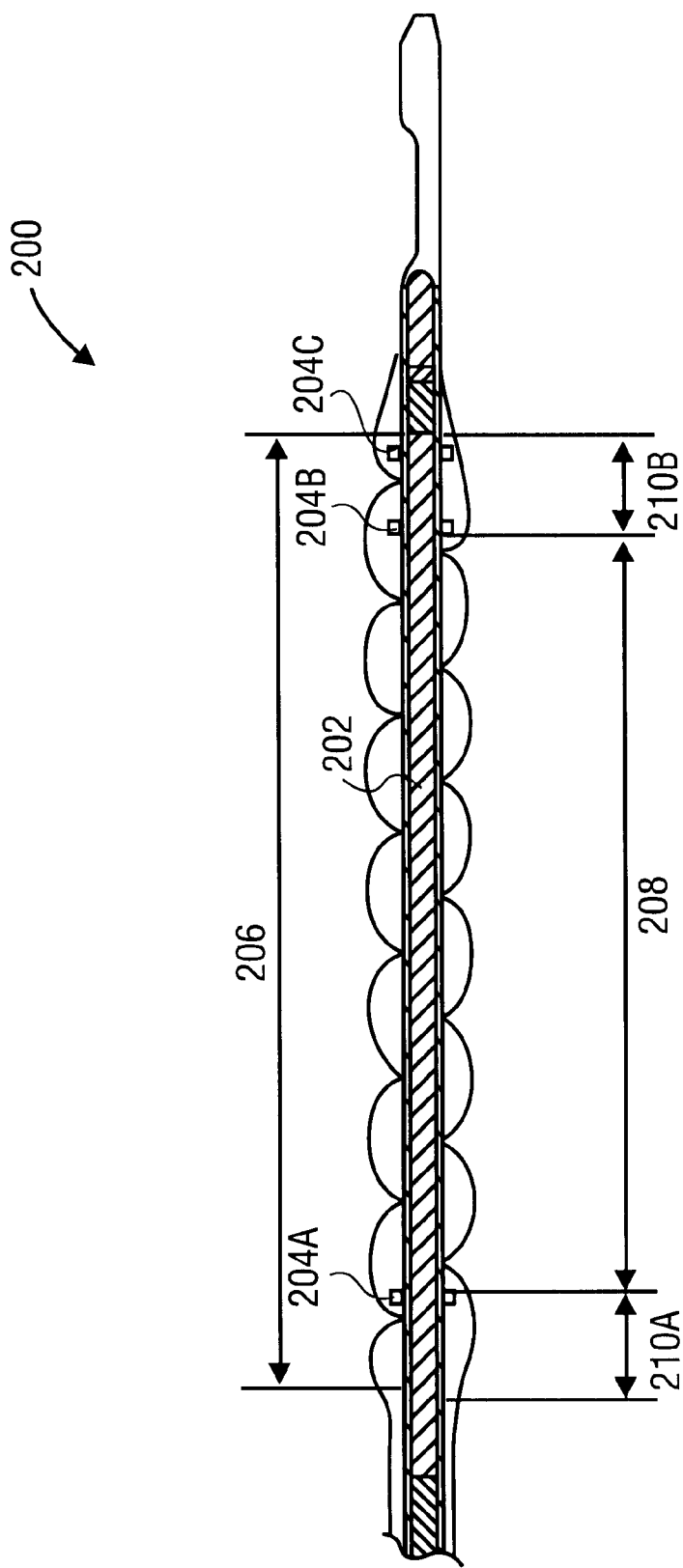
FIG. 14 illustrates a longitudinal cross-sectional view of one embodiment of a radiation delivery system which includes a 3-marker catheter used in conjunction with a radiation source according to the present invention.

FIG. 14 illustrates a longitudinal cross-sectional view of one embodiment of a radiation delivery system which includes a 3-marker catheter used in conjunction with a radiation source according to the present invention. In this embodiment, the catheter 200 is used in conjunction with a radiation source 202 so that a therapeutic dose of radiation is delivered along a therapeutic treatment length 208. In one embodiment, catheter 200 includes first and second radio-opaque markers 204A and 204B which are spaced a distance apart so as to define a therapeutic treatment length and a third radio-opaque marker 204C located outside the therapeutic treatment length 208. In one embodiment, the catheter 200 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21.

In one embodiment, the radiation source 202 may have radioactive region 206 which includes a therapeutic dose region 208 and proximal and distal sub-therapeutic dose regions 210A and 210B. In one embodiment, the third marker 204C is located a distance distal to the distal marker 204B. In one embodiment, the distance may be equal to the length of the distal sub-therapeutic dose region 210B, and may further include a length for positioning tolerances as discussed in reference to FIG. 3. In this way, the radiation source 202 is positioned within the catheter 200 so that the distal end of the radioactive region 206 just exits the marker 204C so that a therapeutic dose of radiation is delivered along the therapeutic treatment length 208.

RADIATION DELIVERY SYSTEM INCLUDING A 2-MARKER CATHETER AND RADIOACTIVE SOURCE POSITIONED RELATIVE TO A DUMMY SOURCE

FIGS. 15A and 15B illustrate a longitudinal cross sectional view of another embodiment of a radiation delivery system according to the present invention including a 2-marker catheter and a radioactive source wire which is positioned relative to the positioning of a dummy source wire. An inactive dummy source wire is first positioned within the catheter relative to the distal marker, and then an active source wire is positioned relative to the positioning of the dummy source wire.

FIG. 15A illustrates a longitudinal cross sectional view of one embodiment of an inactive dummy source wire positioned within a 2 marker catheter according to the present invention. In one embodiment, the catheter 230 includes radio-opaque proximal and distal catheter markers 232A and 232B that are spaced apart to define a therapeutic treatment length 238. In one embodiment, the catheter 230 may be a centering catheter such as a stepped centering catheter which substantially radially centers the portion of the radioactive source located within therapeutic treatment length within the vessel lumen and offsets portions of the radioactive source located outside the therapeutic treatment length a minimum distance from the vessel wall. An example of a stepped centering catheter is further described herein with reference to FIGS. 17–21. It is to be understood that the catheter 230 may also be another type of centering catheter, or a non-centering catheter.

In one embodiment, an inactive dummy source wire 234 is initially positioned in the catheter 230. In one embodiment, the dummy source wire 234 may be a polymide tube with an inactive end plug of 1 mm NiTi. The dummy source wire 234 may further have a distal radio-opaque marker 236, such as a tungsten band, which may be twice as long as the radio-opaque catheter markers 232A and 232B. The catheter 230 may be connected to a radiation delivery device, such as an automated afterloader device discussed herein with reference to FIG. 16, that advances the dummy source wire 234 within the catheter 230. It is to be understood that the dummy source wire 234 may be also be positioned by devices other than an afterloader or manually.

The dummy source wire 234 is advanced within the catheter 230 until the marker 236 is correctly positioned relative to the distal marker 232B. In one embodiment, the marker 236 may be correctly positioned when it is substantially aligned with the distal marker 232B. The length the dummy source wire 234 is advanced to the correct positioning relative to marker 232B may be termed a first location and is recorded. The first location may be recorded by the afterloader device, manually, or by other means. The dummy source wire 234 is then retracted and a radioactive source wire is then advanced into the catheter 230.

FIG. 15B illustrates a longitudinal cross sectional view of one embodiment of radioactive source wire positioned relative to the positioning of the dummy source wire within the 2 marker catheter of FIG. 15A according to the present invention. After the dummy source wire 234 is retracted, a radioactive source wire 240 is advanced to a second location relative to the first location. In one embodiment, the radioactive source wire 240 may include proximal and distal sub-therapeutic dose regions 244A and 244B and a therapeutic dose region 246 in between. In one embodiment, the radioactive source wire 240 may have the same specifications as the dummy source wire 240, but with the radioactive source material added. Thus, in one embodiment, the radioactive source wire 240 may be a polymide tube with a radiation source of $^{32}$P and a radio-opaque distal source end marker 242. It is to be understood that isotopes other than $^{32}$P may be used in the present invention. Further, a marker 242 is not necessary if the radiation source is visible using the radioimagery system used during the procedure, and the end of the radiation source can be seen.

In one embodiment, the afterloader may advance the radioactive source wire 240 within the catheter 230 so that it overshoots the first location and is then distally retracted to a second location. In one embodiment, the second location may be located a distance distal to the first location equal to at least the distal sub-therapeutic dose region 244B, and may further include a positioning tolerance length. This intentional distal positioning allows the initial distal portion of the therapeutic treatment length to receive a therapeutic dose. In this way a therapeutic dose of radiation is delivered along the therapeutic treatment length.

In another embodiment, a dummy source wire 234 is not required. In this other embodiment, the radioactive source wire 240 is advanced to the distal marker 232B, i.e., to the first location. Once the first location is recorded, the radioactive source wire 240 is then advanced an additional pre-determined length distal to the first location, i.e., to the second location. In one embodiment, the additional pre-determined length may be equivalent to at least the length of the distal sub-therapeutic dose region 244B, and may further include a positioning tolerance length. Once the radioactive source wire 240 has been advanced the pre-determined distance distal to the first location, it may be left in place until a prescribed therapeutic dose of radiation has been delivered along the therapeutic treatment length.

Although the radiation delivery systems described in FIGS. 10–15 have been illustrated using a single radiation source equal to the total radiation source length, it is to be understood that, as earlier discussed, the radiation source used in the systems may be a smaller radiation source length used according to a stepping protocol which creates an effective total radiation source length, so that a therapeutic dose is delivered along the therapeutic treatment length. Additionally, although the inactive dummy radiation source is described above as a dummy source wire, other radiation sources may be used and thus, other inactive versions of those sources may also be used.

RADIATION DELIVERY DEVICE

Figure 16:
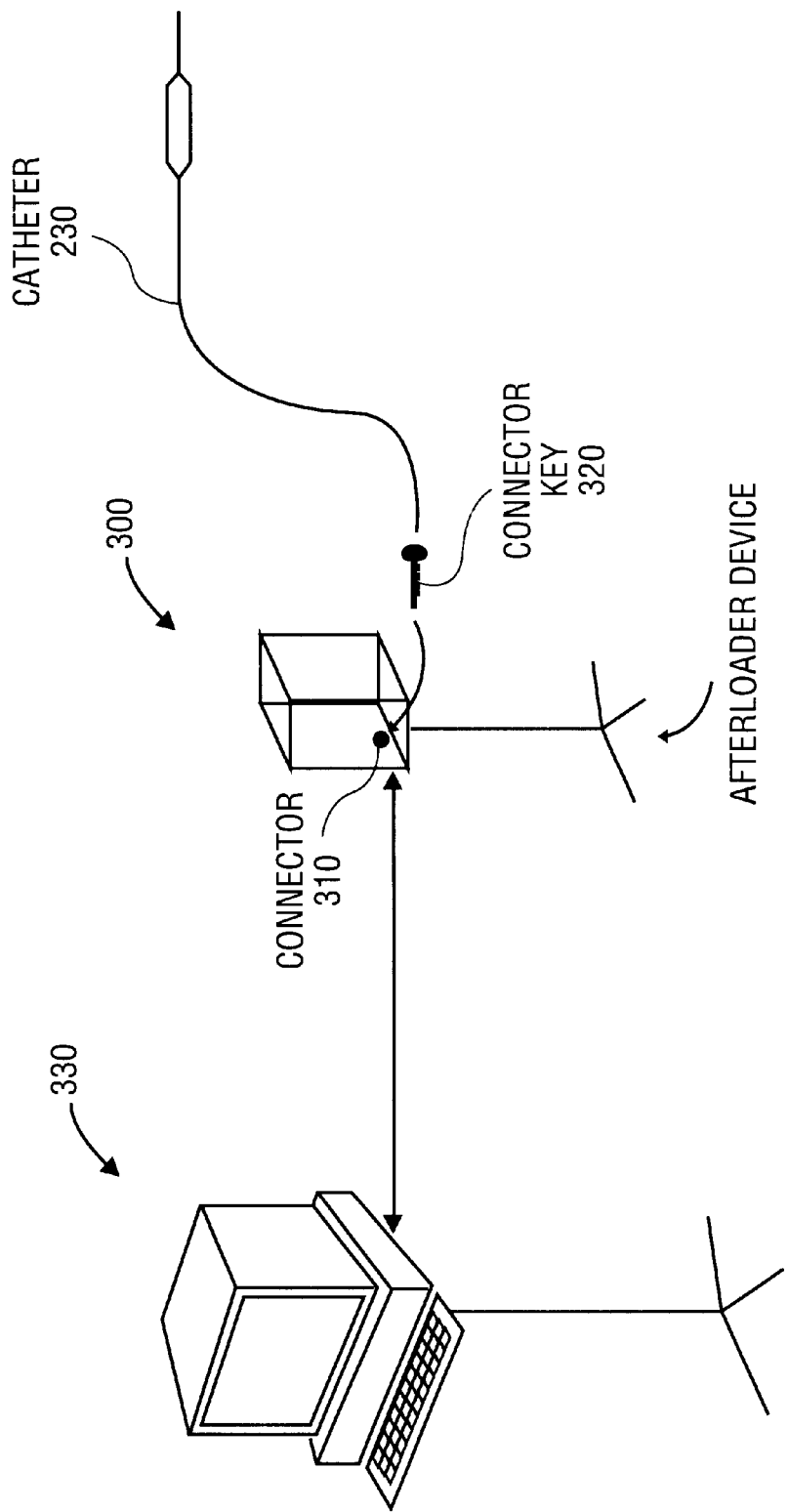
FIG. 16 illustrates one embodiment of a radiation delivery device for positioning a radiation source wire relative to a dummy source wire according to the present invention.

FIG. 16 illustrates one embodiment of a radiation delivery device for positioning a radiation source wire relative to a dummy source wire according to the present invention. As discussed with reference to FIGS. 15A and 15B the catheter 230 may be connected to a radiation delivery device 300 via a connector 310 to allow advancement and retraction of an inactive radiation source, such as the inactive dummy wire 234, and of an active radiation source, such as the radioactive source wire 240, within the catheter 230. The catheter 230 may have a connector key 320 which attaches to connector 310. In one embodiment, the connector key 320 may provide parameters pertaining to the catheter 230 to the afterloader device 300. In one embodiment the catheter 230 may be a catheter as discussed with reference to FIGS. 15A and 15B. In one embodiment, the radiation delivery device 300 may be an afterloader which includes an inactive radiation source which is positionable within the catheter 230 and a means for positioning the inactive radiation source at a first location within the catheter 230. Additionally, the radiation delivery device 300 includes an active radiation source positionable within the catheter 230 and a means for positioning an active radiation source relative to the first location after the inactive radiation source is retracted from the catheter 230. Further, the radiation delivery device 300 includes a means for recording the first location.

The radiation delivery device 300 may also include a means for manually inputting data; a means for receiving manually input data; a means for outputting data for display; and a means for displaying data. In one embodiment these means may embodied as a computer system 330 having a keyboard, display, CPU with memory and input and output ports to allow communication between the radiation delivery device 300 and the computer system 330.

STEPPED CENTERING CATHETER

As discussed with regard to the various embodiments of the present invention described above with reference to FIGS. 3–16, a radiation source may be positioned within a catheter relative to radio-opaque markers so that a therapeutic dose of radiation is delivered along a therapeutic treatment length. The catheter may also substantially center a portion of the radioactive source within the vessel along the therapeutic treatment length so that an approximately uniform dose of radiation is delivered. However, in order to deliver the therapeutic dose within the therapeutic treatment length, portions of the radioactive source may extend beyond the centered therapeutic treatment length. Extending the radiation source beyond the centered therapeutic treatment length may result in overdosing the vessel wall if portions of the extended radiation source become positioned too close to a vessel wall. Thus, a stepped centering catheter having a stepped centering balloon may be used to substantially center a portion of the radioactive source within the vessel along the therapeutic treatment length and to mitigate overdosing of the vessel wall by offsetting the portions of the radiation source that extend outside the therapeutic treatment length a minimum distance from the vessel wall.

Figure 17:
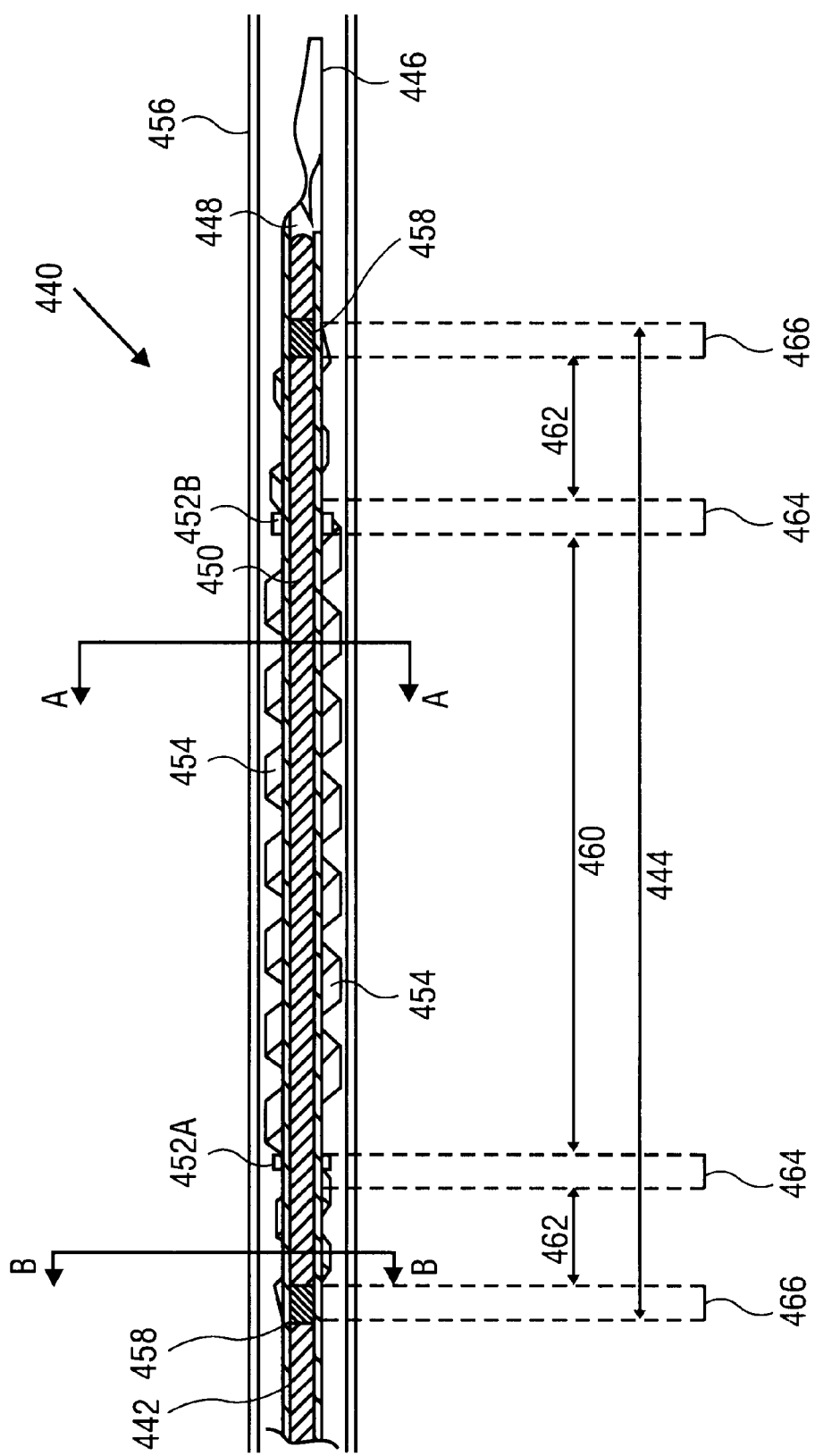
FIG. 17 illustrates a longitudinal cross-sectional view of a stepped centering catheter having a stepped centering balloon that may be used with the present invention.

FIG. 17 illustrates a longitudinal cross-sectional view of one embodiment of a stepped centering catheter having a stepped centering balloon that may be used with the present invention. The stepped centering balloon catheter 440 illustrated in FIG. 17 includes an elongate, tubular shaft 442 and a stepped centering balloon segment 444. The shaft 442 has a proximal end to allow introduction of a radioactive source 450, such as a radioactive source wire, into the shaft lumen 448, and may have an open or closed distal tip 446. The radioactive source 450 may have proximal and distal radio-opaque source markers 458 to enhance visualization by radioimagery systems, such as fluoroscopy. The radio-opaque source markers 458 may be formed of tungsten, or of other materials, such as gold, or platinum.

The proximal end of the stepped centering balloon catheter 440 may be connected to a radiation source delivery device such as an afterloader, or other device, for advancing a radiation source within the stepped centering balloon catheter 440. For example, an afterloader produced by Guidant Corporation, Houston, Tex., may be used. If an afterloader is used in conjunction with the present invention, the stepped centering balloon catheter 440 may be connected to the afterloader system utilizing a key connector that allows the afterloader system to identify the particular characteristics of the stepped centering catheter.

As illustrated in FIG. 17, the stepped centering balloon segment 444 may be formed as a continuous, inflatable helical balloon that forms lobes 454 around the shaft 442. An inflation lumen may be provided at the proximal end of the stepped centering balloon segment 444 to allow inflation from a pump or other inflation apparatus.

The stepped centering balloon segment 444 may include a central balloon segment 460 of a first diameter and offset balloon segments 462 of a smaller, second diameter. It is to be noted that when inflated, the nature of a helical balloon is such that as the lobes 454 advance and spiral around the length of the shaft 442, an effective diameter is created which limits the radial positioning of the radiation source 450 within the vessel 456.

The stepped centering balloon catheter 440 may have proximal and distal radio-opaque markers 452A and 452B attached to the shaft 442 that delineate the proximal and distal ends of the central balloon segment 460. In this way, the markers 452A and 452B delineate the portion of the radiation source 450 that is substantially centered within the vessel lumen.

In use, the stepped centering balloon catheter 440 is selected so that when properly inflated, the first effective diameter of the central balloon segment 460 is sized to be just large enough to compliantly engage the walls of vessel 456 and to substantially center the shaft lumen 448, and, thus, a portion of the radiation source 450, within the lumen of the vessel 456. For example, the first effective diameter of the central balloon segment 460 may be determined to substantially center a portion of the radiation source 450 which may deliver a therapeutic dose of 20 Gy at 1 mm into the vessel. The first effective diameter of the central balloon segment 460 is stepped down to the smaller, second effective diameter of the offset balloon segments 462 across first steps 464. In this example, the first effective diameter of the central balloon segment 460 is continued to the interior edges of the markers 452A and 452B, i.e., the therapeutic treatment length. Thus, the central balloon segment 460 substantially centers the therapeutic dose region of radiation source 450 between the markers 452A and 452B. The first effective diameter is then gradually tapered to the second effective diameter along the length of the first steps 464.

The second effective diameter of the offset balloon segments 462 is sized to offset portions of the radiation source 450 which extend beyond the central balloon segment 460 within a region having a minimum offset distance from the vessel wall. In this way, the radiation dose delivered to the vessel wall from the portions of the radiation source 450 that extend beyond the central balloon segment 460 may be controlled to prevent overdosing the vessel. For example, the second effective diameter of the offset balloon segments 462 may be determined to limit the radiation dose delivered by the portions of the radiation source 450 which extend beyond the central balloon segment 460, as discussed above, to 100 Gy or less at the vessel surface. Thus, the offset balloon segments 462 offset sub-therapeutic portions of the radiation source 450 that extend outside the markers 452A and 452B to prevent overdosing the vessel. Additionally, although the offset balloon segments 462 may extend beyond the therapeutic treatment length of the vessel, the smaller, second effective diameter should not cause or exacerbate stretches or tears in the vessel, thus mitigating further damage to the vessel.

It is to be noted that although the present embodiment is shown having offset balloon segments 462 both proximal and distal to the central balloon segment 460, in alternative embodiments, the present invention may have only a proximal offset balloon segment 462 or a distal offset balloon segment 462 with the corresponding first and second steps. In these embodiments, the opposite side of the central balloon segment 460 without an offset balloon segment 462 may retain a first step 464 tapering the first effective diameter to the diameter of the shaft 442. In other embodiments, the diameter of the shaft 442 may be sufficiently similar to the first effective diameter so that the opposite side of the central balloon segment 460 without an offset balloon segment 462 may not require a first step 464.

The second effective diameter of the offset balloon segments 462 is stepped down to the smaller diameter of the shaft 442 across second steps 466. In this example, the second effective diameter of the offset balloon segments 462 is continued to the end of the radiation source 450. The second effective diameter is then gradually tapered to the diameter of the shaft 442 along the length of the second steps 466. The first steps 464 and second steps 466 allow for a gradual increase and reduction in the effective diameters created by the helical lobes 454 as the stepped centering balloon catheter 440 is positioned within the vessel. The gradual tapering is provided to allow the vessel walls to gradually respond to the differences in diameters of the centering balloon catheter 440 structure in an attempt to mitigate additional damage to the vessel.

The stepped centering balloon segment 444 may be fabricated using standard techniques well known to those of ordinary skill in the art. In one embodiment, the stepped centering balloon segment 444 may be fabricated using a shape mold and materials of relatively high strength that will expand to a fixed diameter when inflated, such as relatively high strength polymers, i.e., nylon, polyester, or polyvinyl acetate or polyethylene. The stepped centering balloon segment 444 is attached to the shaft 442 by bonds that are located at the ends of the stepped centering balloon segment 444. The bonds may be thermal or ultrasonic welds, adhesive or solvent bonds, or may be formed by other conventional means well known to those of ordinary skill in the art.

The radio-opaque markers 452A and 452B may be gold, platinum, or other materials commonly viewable using radioimagery systems, such as fluoroscopy. The radio-opaque markers 452A and 452B may be attached to the shaft 442 by conventional means well known to those of ordinary skill in the art. In one embodiment, the radio-opaque markers 452A and 452B may be attached to the shaft 442 immediately outside the central balloon segment 460 to delineate the endpoints of the central balloon segment 460. It will be appreciated that when used with the present invention, the length of the central balloon segment 460 may be determined according to the therapeutic treatment length calculated for a particular vessel. In this way, using radio-imagery systems, the radio-opaque markers 452A and 452B provide a visual landmark of the portion of the radioactive source 450 that is substantially centered within the vessel.

Figure 18:
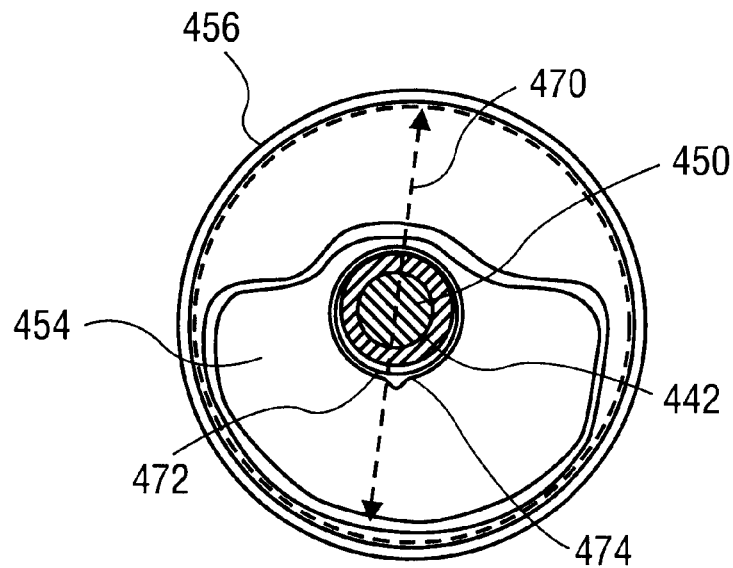
FIG. 18 illustrates a transverse cross-sectional view of the stepped centering catheter of FIG. 17 taken at A—A.

FIG. 18 illustrates a transverse cross-sectional view of the stepped centering catheter of FIG. 17 taken at A—A. In the illustration, the radiation source 450 within the shaft 442 is substantially centered within the lumen of the vessel 456 due to the first effective diameter 470 created by the helical lobes 454 of the central balloon segment 460. This allows for an approximately uniform dose of radiation to be delivered to the vessel wall along the therapeutic treatment length. In the illustration, a support mandrel lumen 472 is shown attached to the shaft 442 to allow insertion of a support mandrel 474. The support mandrel 474 may be introduced proximal to the stepped centering balloon segment 444 and may run substantially the length of stepped centering segment 444 and terminate at the distal tip 446. The support mandrel lumen 472 and support mandrel 474 may be formed and attached to the shaft 442 using methods well known to those of ordinary skill in the art. It is to be understood that other embodiments without a support mandrel lumen 472 and support mandrel 474 may also be used. Further it is to be understood that the present invention may also be formed with a guidewire lumen for accepting a guidewire, but that the use of a guidewire is not necessary, and is not meant to limit the scope of the present invention.

Figure 19:
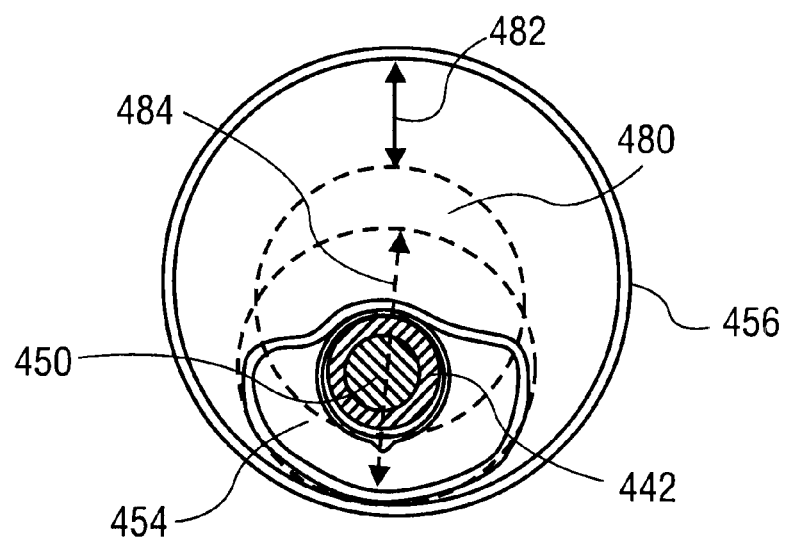
FIG. 19 illustrates a transverse cross-sectional view of the stepped centering catheter of FIG. 17 taken at B—B.

FIG. 19 illustrates a transverse cross-sectional view of the stepped centering catheter of FIG. 17 taken at B—B. In this embodiment, the radiation source 450 is located within the shaft 442 and is maintained within a region 480 having a minimum offset distance 482 from the vessel wall. The minimum offset distance 482 is provided by the smaller, second effective diameter 484 created by the helical lobes 454 in the offset balloon segments 462. Thus, although the portions of the radiation source 450 in the offset balloon segments 462 have more area of movement within the vessel 456 than the portion of the radiation source 450 within the central balloon segment 460, they are constrained to the region 480. The region 480 is maintained at the offset distance 482 so that the radiation dose delivered to the vessel wall is equal to or less than a dosage determined by the minimum offset distance 482. For example, the second effective diameter 484 may be determined to provide a minimum offset distance 482 from the vessel wall so that the radiation dose delivered to the vessel is 100 Gy or less at the vessel surface. Depending upon the radiation source, and the desired maximum radiation dose, the offset distance 482 may be varied by varying the second effective diameter 484. In this way, the offset balloon segments 462 mitigate overdosing of the vessel by portions of the radiation source 450 that extend beyond the therapeutic treatment length.

Figure 20:
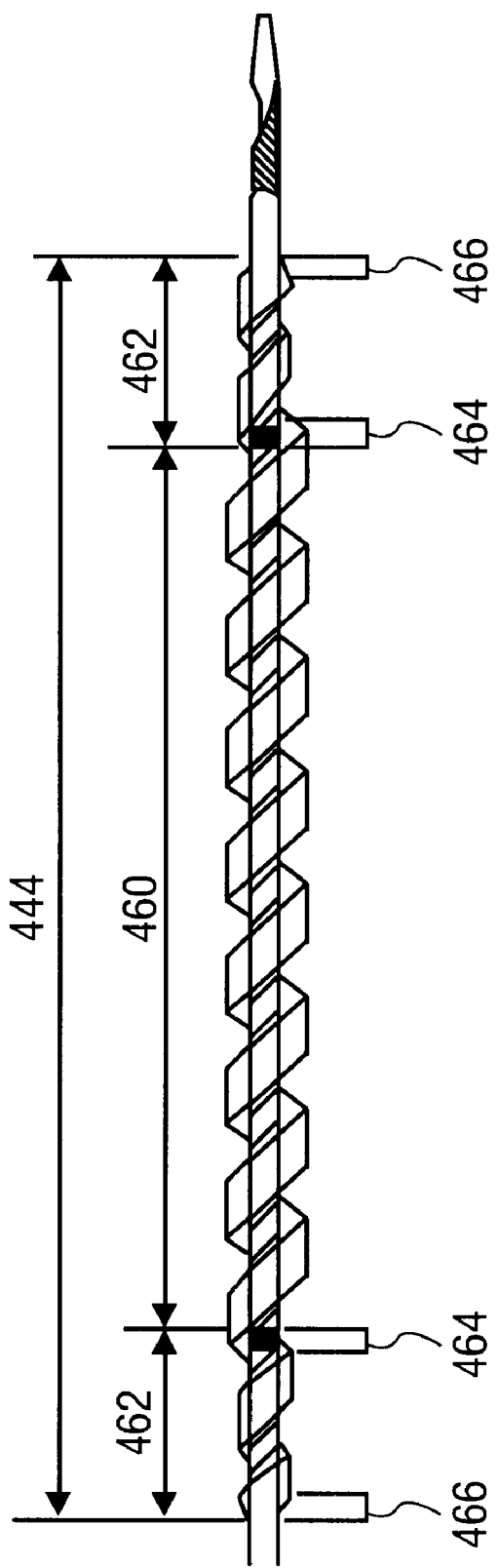
FIG. 20 illustrates an external side view of the stepped centering catheter of FIG. 17.

FIG. 20 illustrates an external side view of the stepped centering catheter of FIG. 17. In this embodiment, the stepped centering balloon segment 444 may have a 32 mm length central balloon segment 460, 1 mm length first steps 464, 5 mm length offset balloon segments 462, and 1 mm length second steps 466.

In another embodiment, the stepped centering balloon segment 444 may have a 52 mm length central balloon segment 460, 1 mm length first steps 464, 5 mm length offset balloon segments 462, and 1 mm length second steps 466.

It is to be understood that the above embodiments are only exemplary, and that other lengths may be used as necessitated by the length of the vessel to be treated and by the length of the portion of the radiation source that is to be radially centered as well as the length of the portion to be offset. For example, in coronary applications, the length of the central balloon segment 460 may range from 12 mm to 90 mm. The length of the offset balloon segments 462 may range from 2 mm to 10 mm. In peripheral applications, the length of the central balloon segment 460 may range from 5 cm to 20 cm. The length of the offset balloon segments 462 may range from 2 mm to 15 mm. However, the above ranges are only exemplary and the lengths will depend on the design of the radiation system and specific isotope used.

To enable utilization of the present invention within vessels of different diameters the above-described embodiments may be formed with a variety of first and second diameters (including effective diameters). The first and second diameters should be selected so that in combination the first diameter substantially centers a portion of the radiation source within the lumen of the vessel along the therapeutic treatment length and the second diameter offsets portions of the radiation source that extend beyond the central balloon segment 460 a minimum distance from the vessel wall. Additionally the minimum offset distance should be determined at a distance which mitigates overdosing a vessel. For example, in the following embodiments the second diameter may be selected to provide a minimum offset distance 482 of a $^{32}P$ radiation source from the vessel so that the radiation dose is 100 Gy or less at the surface of the vessel.

In one embodiment, when inflated, the central balloon segment 460 may have a 2.5 mm outer effective first diameter 470 and the offset balloon segments 462 may have 1.75 mm outer effective second diameters 484.

In a second embodiment, when inflated, the central balloon segment 460 may have a 3.0 mm outer effective first diameter 470 and the offset balloon segments 462 may have 2.0 mm outer effective second diameters 484.

In a third embodiment, when inflated, the central balloon segment 460 may have a 3.5 mm outer effective first diameter 470 and the offset balloon segments 462 may have 2.25 mm outer effective second diameters 484.

In a fourth embodiment, when inflated, the central balloon segment 460 may have a 4.0 mm outer effective first diameter 470 and the offset balloon segments 462 may have 2.5 mm outer effective second diameters 484.

It is to be understood that the above embodiments are exemplary and that other diameters may be used. For example, in coronary applications the outer effective first diameter 470 may range in size from 2.0 mm to 4.0 mm. The outer effective second diameters 484 may range from 1.5 mm to 3.0 mm. In peripheral applications, the outer effective first diameter 470 may range in size from 4.0 mm to 10 mm. The outer effective second diameters 484 may range from 2.0 mm to 7.0 mm. The above ranges are only exemplary and other diameters may be used dependent in large part upon the isotope selected.

Figure 21:
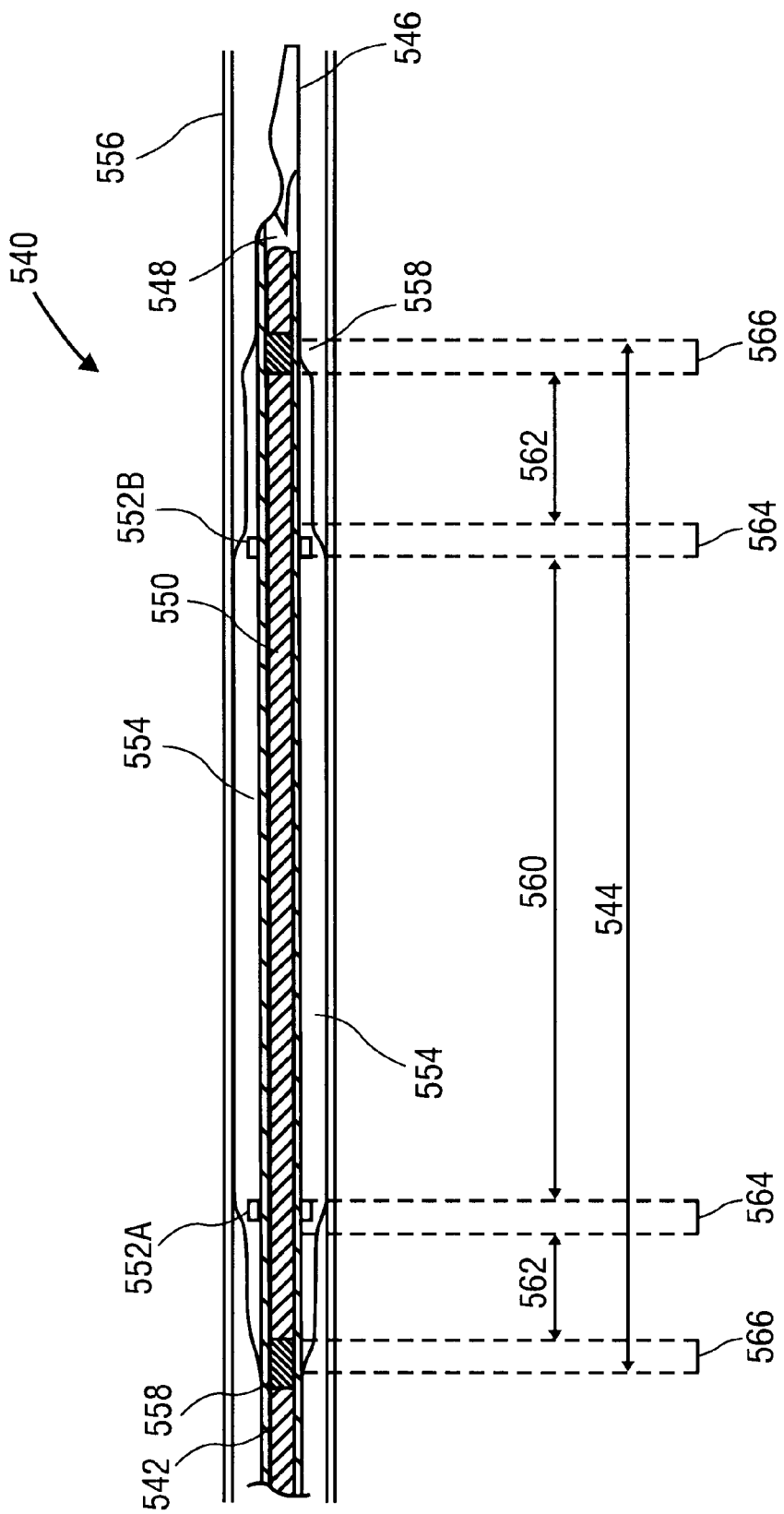
FIG. 21 illustrates a longitudinal cross-sectional view of another embodiment of a stepped centering catheter having a stepped centering fluted balloon that may be used with the present invention.

FIG. 21 illustrates a longitudinal cross-sectional view of another embodiment of a stepped centering catheter having a stepped centering fluted balloon that may be used with present invention. In the embodiment of FIG. 21, the stepped centering catheter may be a stepped centering fluted balloon catheter. The stepped centering fluted balloon catheter 540 includes an elongate, tubular shaft 542 and a stepped centering fluted balloon segment 544. The shaft 542 has a proximal end to allow introduction of a radioactive source 550, such as a radioactive source wire, into the shaft lumen 548, and may have an open or closed distal tip 546. The radioactive source 550 may have proximal and distal radio-opaque source markers 558 to enhance visualization by radioimagery systems, such as fluoroscopy. The radio-opaque source markers 558 may be formed of tungsten, or of other materials, such as gold, or platinum.

The proximal end of the stepped centering fluted balloon catheter 540 may be connected to a radiation source delivery device such as an afterloader, or other device, for advancing a radiation source within the stepped centering fluted balloon catheter 540. For example, an afterloader produced by Guidant Corporation, Houston, Tex., may be used. If an afterloader is used in conjunction with the present invention, the stepped centering fluted balloon catheter 540 may be connected to the afterloader system utilizing a key connector that allows the afterloader system to identify the particular characteristics of the stepped centering catheter.

As illustrated in FIG. 21, the stepped centering fluted balloon segment 544 may be formed as a continuous, inflatable fluted balloon including a plurality of individual fluted lobes 554 spaced around the shaft 542. An inflation lumen may be provided at the proximal end of the stepped centering fluted balloon segment 544 to allow inflation from a pump or other inflation apparatus.

The stepped centering fluted balloon segment 544 may include a central fluted balloon segment 560 of a first diameter and offset fluted balloon segments 562 of a smaller, second diameter. It is to be noted that when inflated, the nature of a fluted balloon is such that together the individual fluted lobes 554 create an effective diameter which limits the radial positioning of the radiation source 550 within the vessel 556.

The stepped centering fluted balloon catheter 540 may have proximal and distal radio-opaque markers 552A and 552B attached to the shaft 542 that delineate the proximal and distal ends of the central fluted balloon segment 560. In this way, the markers 552A and 552B delineate the portion of the radiation source 550 that is substantially centered within the vessel lumen.

In use, the stepped centering fluted balloon catheter 540 is selected so that when properly inflated, the first effective diameter of the central fluted balloon segment 560 is sized to be just large enough to compliantly engage the walls of vessel 556 and to substantially center the shaft lumen 548, and, thus, a portion of the radiation source 550, within the lumen of the vessel 556. For example, the first effective diameter of the central fluted balloon segment 560 may be determined to substantially center a portion of the radiation source 550 which may deliver a therapeutic dose of 20 Gy at 1 mm into the vessel. The first effective diameter of the central fluted balloon segment 560 is stepped down to the smaller, second effective diameter of the offset fluted balloon segments 562 across first steps 564. In this example, the first effective diameter of the central fluted balloon segment 560 is continued to the interior edges of the markers 552A and 552B, i.e., the therapeutic treatment length. Thus, the central fluted balloon segment 560 substantially centers the therapeutic dose region of radiation source 550 between the markers 552A and 552B. The first effective diameter is then gradually tapered to the second effective diameter along the length of the first steps 564.

The second effective diameter of the offset fluted balloon segments 562 is sized to offset portions of the radiation source 550 which extend beyond the central fluted balloon segment 560 within a region having a minimum offset distance from the vessel wall. In this way, the radiation dose delivered to the vessel wall from the portions of the radiation source 550 that extend beyond the central fluted balloon segment 560 may be controlled to prevent overdosing the vessel. For example, the second effective diameters of the offset fluted balloon segments 562 may be determined to limit the radiation dose delivered by the portions of the radiation source 550 which extend beyond the central fluted balloon segment 560, as discussed above, to 100 Gy or less at the vessel surface. Thus, the offset fluted balloon segments 562 offset sub-therapeutic portions of the radiation source 550 that extend outside the markers 552A and 552B to prevent overdosing the vessel. Additionally, although the offset fluted balloon segments 562 may extend beyond the therapeutic treatment length of the vessel, the smaller, second effective diameter should not cause or exacerbate stretches or tears in the vessel, thus mitigating further damage to the vessel.

It is to be noted that although the present embodiment is shown having offset fluted balloon segments 562 both proximal and distal to the central fluted balloon segment 560, alternative embodiments may have only a proximal offset fluted balloon segment 562 or a distal offset fluted balloon segment 562 with the corresponding first and second steps. In these embodiments, the opposite side of the central fluted balloon segment 560 without an offset fluted balloon segment 562 may retain a first step 564 tapering the first effective diameter to the diameter of the shaft 542. In other embodiments, the diameter of the shaft 542 may be sufficiently similar to the first effective diameter so that the opposite side of the central fluted balloon segment 560 without an offset fluted balloon segment 562 may not require a first step 564.

The second effective diameter of the offset fluted balloon segments 562 is stepped down to the smaller diameter of the shaft 542 across second steps 566. In this example, the second effective diameter of the offset fluted balloon segments 562 is continued to the end of the radiation source 550. The second effective diameter is then gradually tapered to the diameter of the shaft 542 along the length of the second steps 566. The first steps 564 and second steps 566 allow for a gradual increase and reduction in the effective diameters created by the fluted lobes 554 as the stepped centering fluted balloon catheter 540 is positioned within the vessel. The gradual tapering is provided to allow the vessel walls to gradually respond to the differences in diameters of the centering fluted balloon catheter 540 structure in an attempt to mitigate additional damage to the vessel.

The stepped centering fluted balloon segment 544 may be fabricated using standard techniques well known to those of ordinary skill in the art. In one embodiment, the stepped centering fluted balloon segment 544 may be fabricated using a shape mold and materials of relatively high strength that will expand to a fixed diameter when inflated, such as relatively high strength polymers, i.e., nylon, polyester, or polyvinyl acetate or polyethylene. The stepped centering fluted balloon segment 544 is attached to the shaft 542 by bonds that are located at the ends of the stepped centering fluted balloon segment 544. The bonds may be thermal or ultrasonic welds, adhesive or solvent bonds, or may be formed by other conventional means well known to those of ordinary skill in the art.

The radio-opaque markers 552A and 552B may be gold, platinum, or other materials commonly viewable using radioimagery systems, such as fluoroscopy. The radio-opaque markers 552A and 552B may be attached to the shaft 542 by conventional means well known to those of ordinary skill in the art. In one embodiment, the radio-opaque markers 552A and 552B may be attached to the shaft 542 immediately outside the central fluted balloon segment 560 to delineate the endpoints of the central fluted balloon segment 560. It will be appreciated that when used with the present invention, the length of the central fluted balloon segment 560 may be determined according to the therapeutic treatment length calculated for a particular vessel. In this way, using radioimagery systems, the radio-opaque markers 552A and 552B provide a visual landmark of the portion of the radioactive source 550 that is substantially centered within the vessel.

Thus, there has been described several embodiments of a stepped centering balloon which may be used with the present invention for delivery of intravascular radiation therapy in which a portion of a radiation source is substantially centered within the lumen of a vessel along a therapeutic treatment length and portions of the radiation source that extend outside the therapeutic treatment length are constrained within a region that has a minimum offset from the vessel wall.

In one embodiment, the stepped centering balloon includes a central balloon segment of a first effective diameter continuous with smaller offset balloon segments of a second effective diameter located to each side of the central balloon segment. The first effective diameter of the central balloon segment is reduced to the smaller, second effective diameters of the offset balloon segments across first steps, and the second effective diameters of the offset balloon segments are reduced to the shaft diameter of the catheter across second steps.

The first effective diameter substantially centers a portion of a radiation source within a vessel so that a therapeutic dose of radiation may be delivered along a therapeutic treatment length. The second effective diameter constrains portions of a radiation source that extends outside the therapeutic treatment length within a region having a minimum offset from the vessel wall. The first and second steps provide a tapered transition between the different balloon segment diameters and the shaft diameter to mitigate further damage to vessel outside the therapeutic treatment length.

In alternative embodiments, a single offset balloon adjacent to either the proximal or distal end of the central balloon segment may be utilized. In these alternative embodiments, the first effective diameter of the central balloon segment is reduced to the effective diameter of the offset balloon segment across a first step, and the second effective diameter of the offset balloon segment is reduced to the shaft diameter across a second step. The opposite side of the central balloon segment may either be reduced to the shaft diameter across a first step, or may not require a reduction due to the size of the shaft diameter.

It is to be understood that the radio-opaque markers and marker materials discussed with reference to the above examples are merely for illustration, and that other markers, fewer or no markers, and other marker materials may be used. It is to be further understood that when radio-opaque markers are discussed herein, the markers may be other than radio-opaque if viewable using a radioimagery system. Additionally, although the stepped centering balloon catheter was discussed with reference to a $^{32}P$ radiation source, it is to be understood that radiation sources other than $^{32}P$ may be used and that modification of the first and second diameters and minimum offset distances may be required. For example, radiation sources may utilize different isotopes and geometries in addition to those described herein.

Thus, the present invention as described includes methods and apparatuses for positioning a radiation source in vivo relative to radio-opaque markers on a catheter that delineate a therapeutic treatment length, so that a therapeutic dose of radiation is delivered along the therapeutic treatment length.

In one embodiment, the present invention includes a method for determining a total radiation source length necessary to deliver a therapeutic dose of radiation along a therapeutic length.

The present invention further includes methods and devices that visually indicate the therapeutic treatment length utilizing markers, and allow a radiation source to be positioned relative to the markers so that a therapeutic dose is delivered along the therapeutic treatment length. These methods and devices allow the therapeutic dose of radiation to be delivered using a single radiation source length equal to the total radiation source length, or by using a radiation source length according to a stepping protocol that creates an effective total radiation source length.

In one embodiment, the present invention includes methods and devices for positioning an active source wire relative to the positioning of a dummy source wire, where the dummy source wire was initially positioned relative to proximal and a distal catheter markers that defined a therapeutic treatment length.

It is to be understood that the various methods and apparatuses described herein are not limited to stepped centering balloon catheters, and may be used with other centering catheters as well as non-centering catheters. However, the use of other catheters may result in delivery of radiation doses which differ from those described herein.

Further, although a therapeutic dose of radiation may be defined as at least the minimum amount of radiation that will effectively reduce restenosis when delivered to a prescribed location of a vessel, it is to be understood that a therapeutic dose of radiation may be defined at other levels determined for a particular radiotherapy treatment.

It is also to be understood that the markers although described as radio-opaque, need only be visible utilizing a radioimagery system used in the procedure and that the particular examples discussed herein are merely for illustration and that other materials may be used.

Additionally, it is to be understood that although the radiation sources described herein are described as having proximal and distal sub-therapeutic dose regions and a therapeutic dose region in between, other radiation sources that have only one of the sub-therapeutic dose regions in addition to the therapeutic dose region may be used. In these cases the methods and apparatuses described herein would be used accordingly and may require some modification.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A radiation delivery catheter comprising:

an elongate, tubular member having a lumen for receiving a radiation source;

a helical balloon disposed around said elongate, tubular member; and proximal and distal markers attached to said elongate, tubular member, wherein said proximal and distal markers are spaced apart along said elongate, tubular member so as to define a therapeutic treatment length.

2. The catheter of claim 1 wherein said elongate, tubular member substantially radially centers said therapeutic treatment length within a vessel lumen.

3. The catheter of claim 1 wherein said helical balloon substantially radially centers said therapeutic treatment length within a vessel lumen.

4. The catheter of claim 1 further comprising a centering balloon that substantially radially centers said therapeutic treatment length within a vessel lumen.

5. The catheter of claim 1 wherein said therapeutic treatment length is the region in which a therapeutic dose of radiation is delivered.

6. The catheter of claim 5 wherein a therapeutic dose of radiation is at least the minimum amount of radiation that will effectively reduce restenosis when delivered to a prescribed location of vessel.

7. The catheter of claim 1, wherein said distal marker is spaced a distance proximal to a position of said lumen, said distance being at least a distal length of said radiation source in which a sub-therapeutic dose of radiation is delivered.

8. A radiation delivery catheter comprising:

an elongate, tubular member having a dead-end lumen for receiving a radiation source;

a proximal marker and a distal marker attached to said elongate, tubular member, wherein said proximal and distal markers are spaced apart along said elongate, tubular member so as to define a therapeutic treatment length, said distal marker being spaced a distance proximal to said dead-end lumen, said distance being at least the distal length of the radiation source in which a sub-therapeutic dose of radiation is delivered.

9. The catheter of claim 8 wherein said distance further includes a length defined by one or more positioning tolerances.

10. The catheter of claim 8 wherein said elongate, tubular member substantially radially centers said therapeutic treatment length within a vessel lumen.

11. The catheter of claim 8 further comprising a centering mechanism that substantially radially centers said therapeutic treatment length within a vessel lumen.

12. The catheter of claim 8 further comprising a centering balloon that substantially radially centers said therapeutic treatment length within a vessel lumen.

* * * * *

UNITED STATES PATENT AND TRADEMARK OFFICE
CERTIFICATE OF CORRECTION

PATENT NO.    : 6,582,417 B1
DATED         : June 24, 2003
INVENTOR(S)   : Ledesma et al.

It is certified that error appears in the above-identified patent and that said Letters Patent is hereby corrected as shown below:

Title page,
Item [56], References Cited, OTHER PUBLICATIONS,
"Michael Haude," reference, please delete both instances of "Ballon" and insert
-- Balloon --.
"Richard E. Kunts," reference, please delete "Ballon" and insert -- Balloon --.
"Louis G. Martin," reference, please delete "Application" and insert -- Applications --.
"Louis G. Martin," reference, (second occurrence), please delete "81-81" and insert
-- 81-82 --.

Signed and Sealed this

Sixth Day of April, 2004

JON W. DUDAS
*Acting Director of the United States Patent and Trademark Office*